US012390455B2

(12) United States Patent
Honma

(10) Patent No.: US 12,390,455 B2
(45) Date of Patent: Aug. 19, 2025

(54) EZH1/2 DUAL INHIBITOR-CONTAINING PHARMACEUTICAL COMPOSITION TO BE USED AS A COMBINATION DRUG

(71) Applicant: DAIICHI SANKYO COMPANY, LIMITED, Tokyo (JP)

(72) Inventor: Daisuke Honma, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 977 days.

(21) Appl. No.: 17/296,460

(22) PCT Filed: Nov. 29, 2019

(86) PCT No.: PCT/JP2019/046794
§ 371 (c)(1),
(2) Date: May 24, 2021

(87) PCT Pub. No.: WO2020/111234
PCT Pub. Date: Jun. 4, 2020

(65) Prior Publication Data
US 2021/0393601 A1 Dec. 23, 2021

(30) Foreign Application Priority Data
Nov. 29, 2018 (JP) ................. 2018-223780

(51) Int. Cl.
*A61P 35/00* (2006.01)
*A61K 31/167* (2006.01)
*A61K 31/282* (2006.01)
*A61K 31/337* (2006.01)
*A61K 31/4045* (2006.01)
*A61K 31/44* (2006.01)
*A61K 31/443* (2006.01)
*A61K 31/454* (2006.01)
*A61K 31/4745* (2006.01)
*A61K 31/475* (2006.01)
*A61K 31/502* (2006.01)
*A61K 31/505* (2006.01)
*A61K 31/506* (2006.01)
*A61K 31/513* (2006.01)
*A61K 31/517* (2006.01)
*A61K 31/519* (2006.01)
*A61K 31/573* (2006.01)
*A61K 31/635* (2006.01)
*A61K 31/69* (2006.01)
*A61K 31/704* (2006.01)
*A61K 31/7048* (2006.01)
*A61K 31/706* (2006.01)
*A61K 31/7068* (2006.01)
*A61K 39/395* (2006.01)

(52) U.S. Cl.
CPC .......... *A61K 31/443* (2013.01); *A61K 31/167* (2013.01); *A61K 31/282* (2013.01); *A61K 31/337* (2013.01); *A61K 31/4045* (2013.01); *A61K 31/44* (2013.01); *A61K 31/454* (2013.01); *A61K 31/4745* (2013.01); *A61K 31/475* (2013.01); *A61K 31/502* (2013.01); *A61K 31/505* (2013.01); *A61K 31/506* (2013.01); *A61K 31/513* (2013.01); *A61K 31/517* (2013.01); *A61K 31/519* (2013.01); *A61K 31/573* (2013.01); *A61K 31/635* (2013.01); *A61K 31/69* (2013.01); *A61K 31/704* (2013.01); *A61K 31/7048* (2013.01); *A61K 31/706* (2013.01); *A61K 31/7068* (2013.01); *A61K 39/3955* (2013.01); *A61P 35/00* (2018.01)

(58) Field of Classification Search
None
See application file for complete search history.

(56) References Cited

U.S. PATENT DOCUMENTS

2017/0073335 A1* 3/2017 Kanno .................. A61P 35/00

FOREIGN PATENT DOCUMENTS

| CA | 2942883 A1 * | 9/2015 | .......... A61K 31/443 |
|---|---|---|---|
| CA | 2993605 A1 * | 2/2017 | ............ A61K 31/36 |
| EP | 3 121 175 A1 | 1/2017 | |
| EP | 3 329 917 A1 | 6/2018 | |
| JP | 2018-522874 A | 8/2018 | |
| JP | 2018-524298 A | 8/2018 | |
| WO | WO-2009/006577 A2 | 1/2009 | |
| WO | WO-2013/067296 A1 | 5/2013 | |
| WO | WO-2013/067302 A1 | 5/2013 | |
| WO | WO-2014/055634 A1 | 4/2014 | |
| WO | WO-2014/077784 A1 | 5/2014 | |
| WO | WO-2015/141616 A1 | 9/2015 | |
| WO | WO-2016/201328 A1 | 12/2016 | |
| WO | WO-2017/002064 A1 | 1/2017 | |

(Continued)

OTHER PUBLICATIONS

Van Arnam et al., 2018, Novel insights into the pathogenesis of T-cell lymphomas, Blood, 131, 2320-2330 (Year: 2018).*
Khoja et al., (2015), Pembrolizumab, Journal for Immunotherapy of Cancer, 3, 1-13 (Year: 2015).*
Extended European Search Report issued in corresponding European Patent Application No. 19889712.6 dated Jul. 29, 2022.
Konze et al., "An Orally Bioavailable Chemical Probe of the Lysine Methyltransferases EZH2 and EZH1", ACS Chemical Biology, 2013, pp. 1324-1334.

(Continued)

*Primary Examiner* — Juliet C Switzer
*Assistant Examiner* — Dawanna Shar-Day White
(74) *Attorney, Agent, or Firm* — Foley & Lardner LLP

(57) ABSTRACT

An object of the present invention is to provide a combination drug having an EZH1/2 dual inhibitor in combination with another medical agent and exerting an excellent anticancer effect. Provided is a combination drug having an EZH1/2 dual inhibitor in combination with another medical agent and exerting an excellent anticancer effect.

10 Claims, 9 Drawing Sheets

(56) References Cited

FOREIGN PATENT DOCUMENTS

WO     WO-2017/018499 A1     2/2017

OTHER PUBLICATIONS

Margueron et al., "EZH1 nd EZH2 maintain repressive chromatin through different mechanisms", PubMed Central, HHMI Howard Hughes Medical Institute, Mol Cell. Nov. 2, 20081, 32(4), pp. 503-518.

Office Action issued in corresponding Brazilian Patent Application No. 112021010194 dated Oct. 24, 2023 (6 pages).

International Searching Authority, "International Search Report," issued in connection with International Patent Application No. PCT/JP2019/046794, dated Feb. 4, 2020.

International Searching Authority, Written Opinion, issued in connection with International Patent Application No. PCT/JP2019/046794, dated Feb. 4, 2020.

Lund et al., "EZH2 in normal and malignant hematopoiesis", Leukemia, 2014, vol. 28, pp. 44-49, 2014 Macmillan Publishers Limited.

Shen et al., "EZH1 Mediates Methylation on Histone H3 Lysine 27 and Complements EZH2 in Maintaining Stem Cell Identity and Executing Pluripotency", Molecular Cell, Nov. 21, 2008, vol. 32, No. 4, pp. 491-502, 2008 Elsevier Inc.

Sparmann et al., "Polycomb silencers control cell fate, development and cancer", Nature Reviews | Cancer, Nov. 2006, vol. 6, pp. 846-856, 2006 Nature Publishing Group.

Office Action issued in connection with Chinese Appl. No. 201980078932.9 dated Jul. 13, 2024.

\* cited by examiner

[Figure 1]
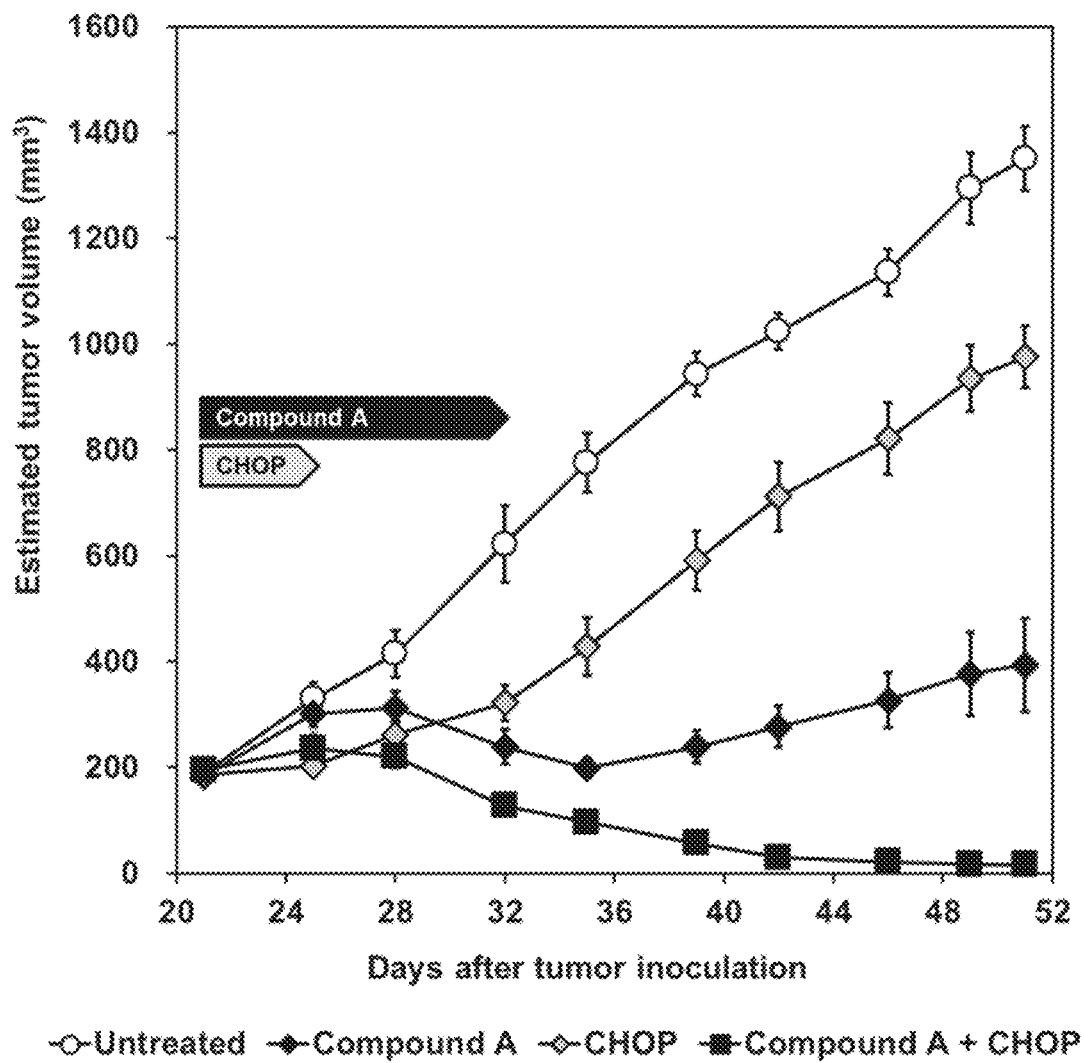

[Figure 2]
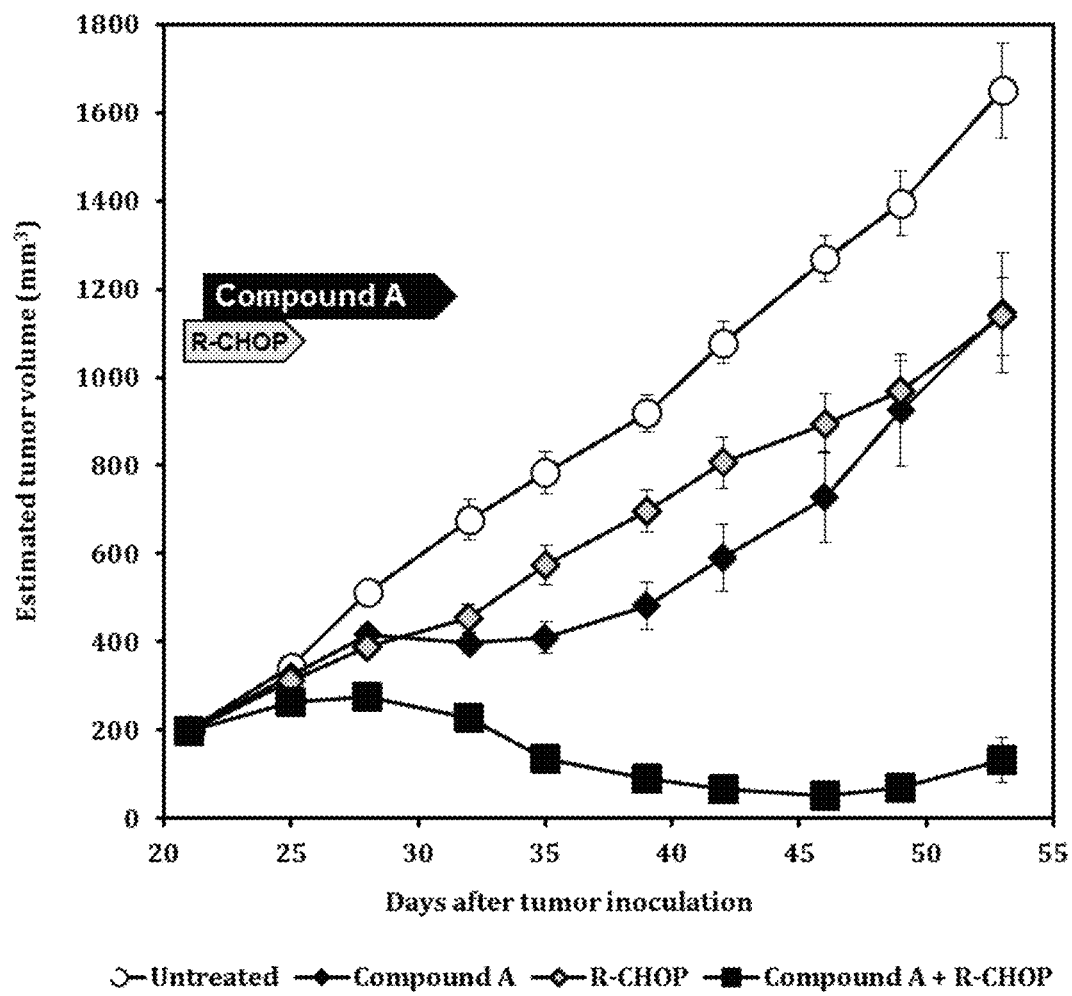

[Figure 3]
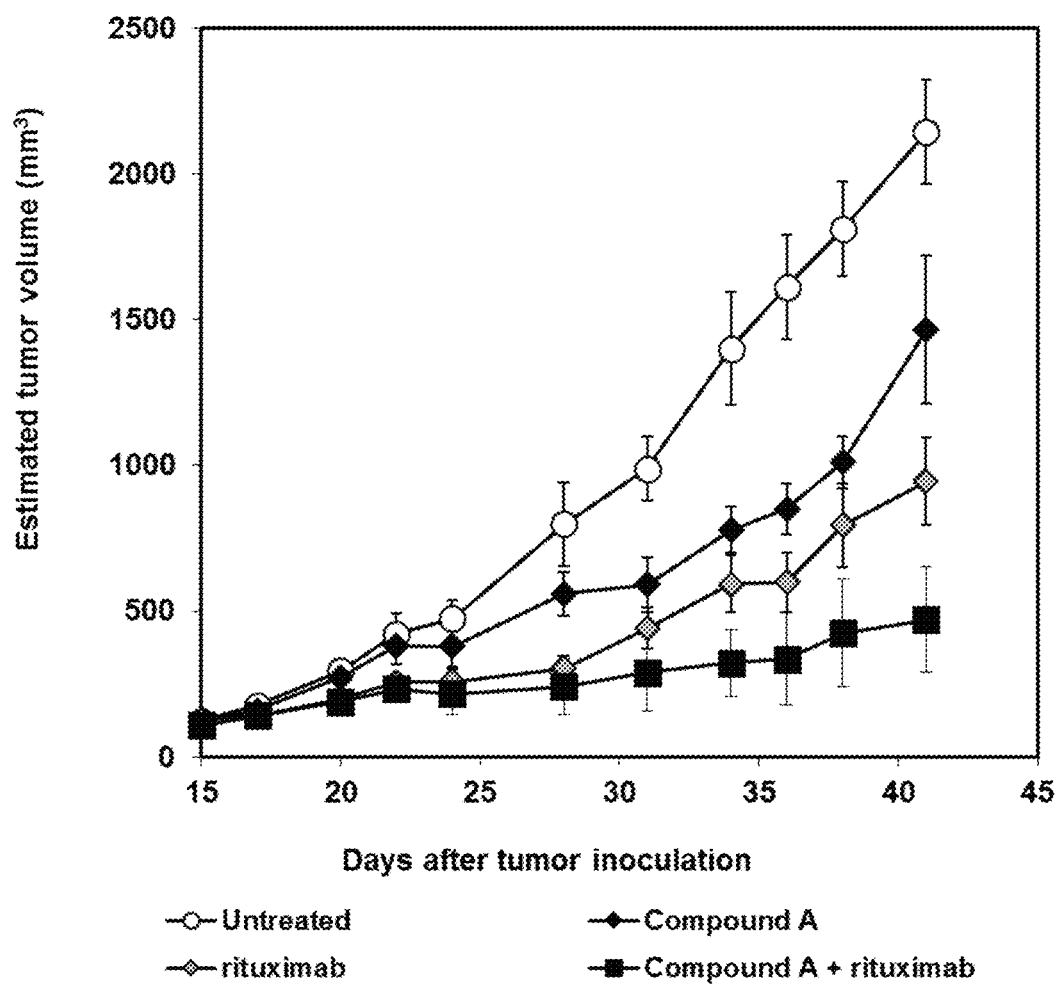

[Figure 4]
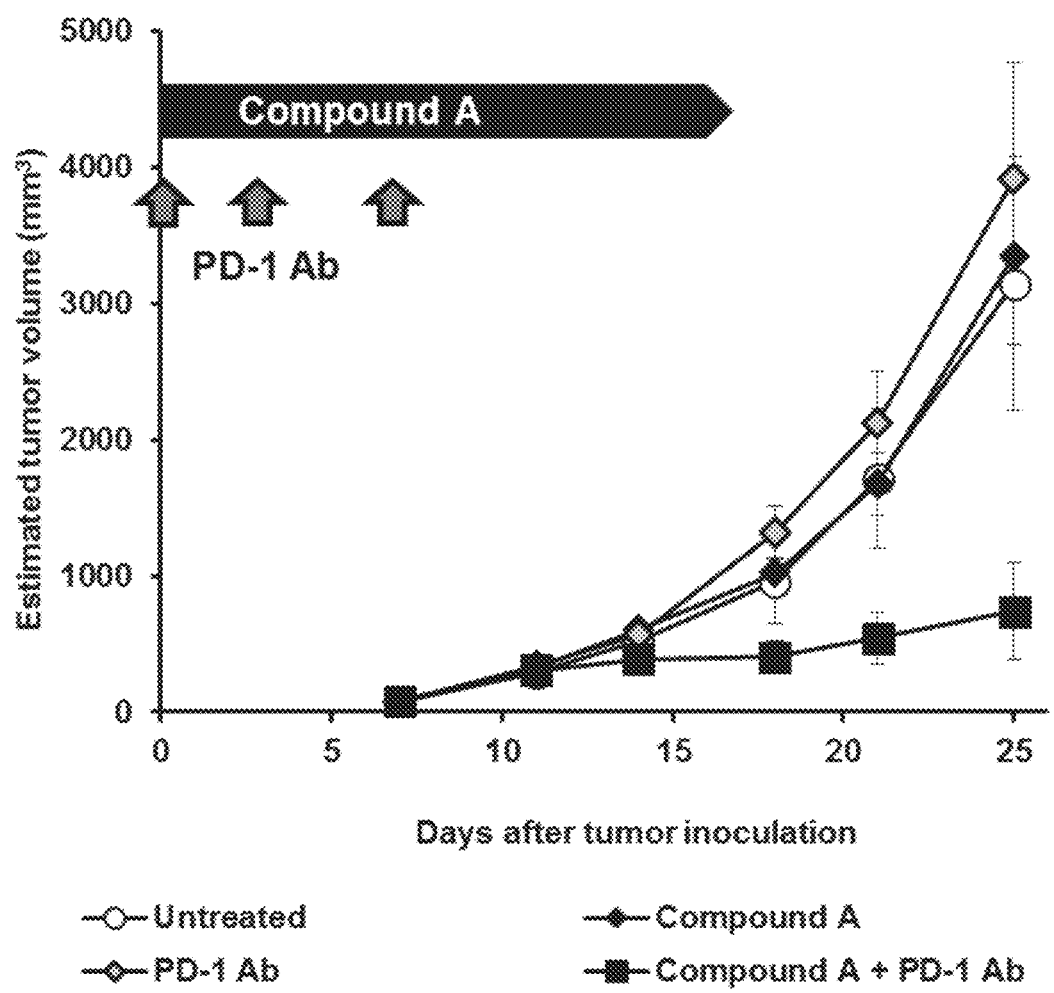

[Figure 5]
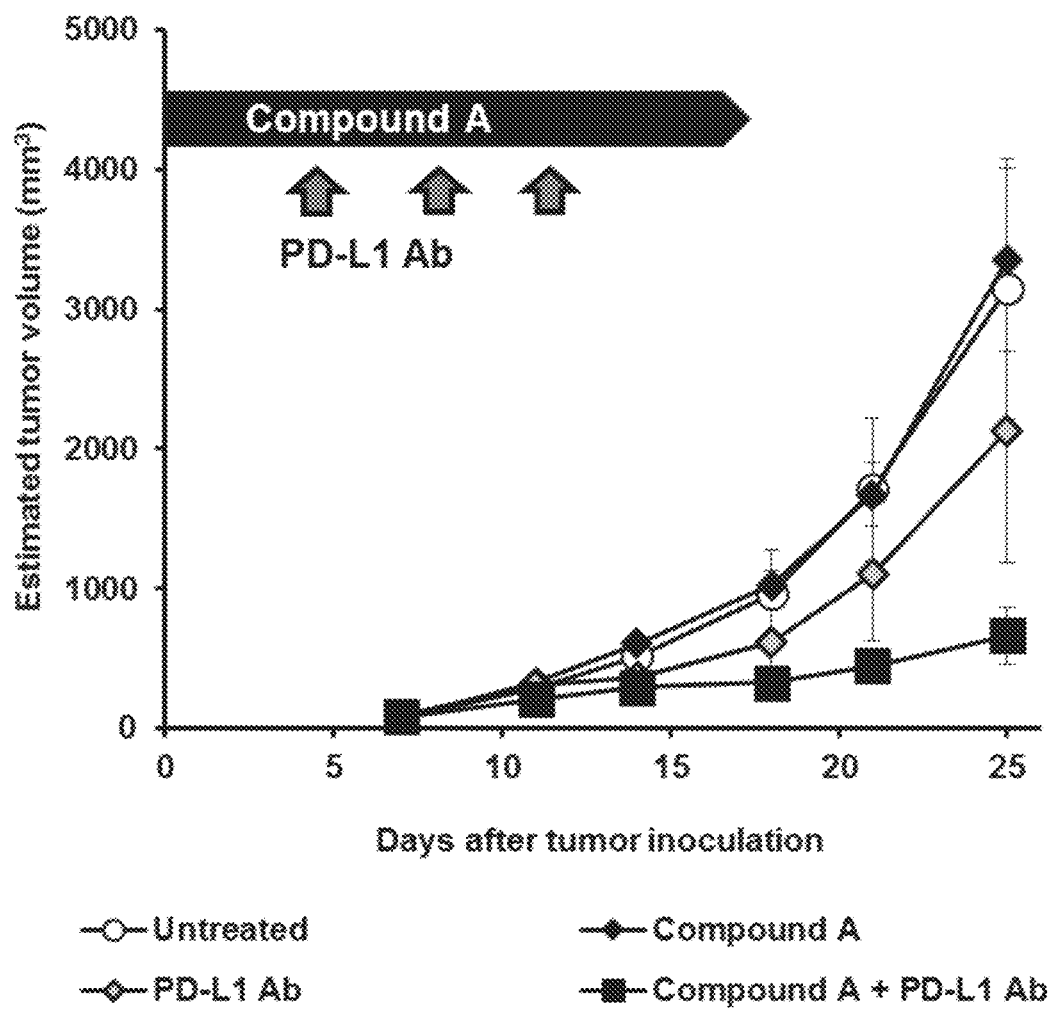

[Figure 6]
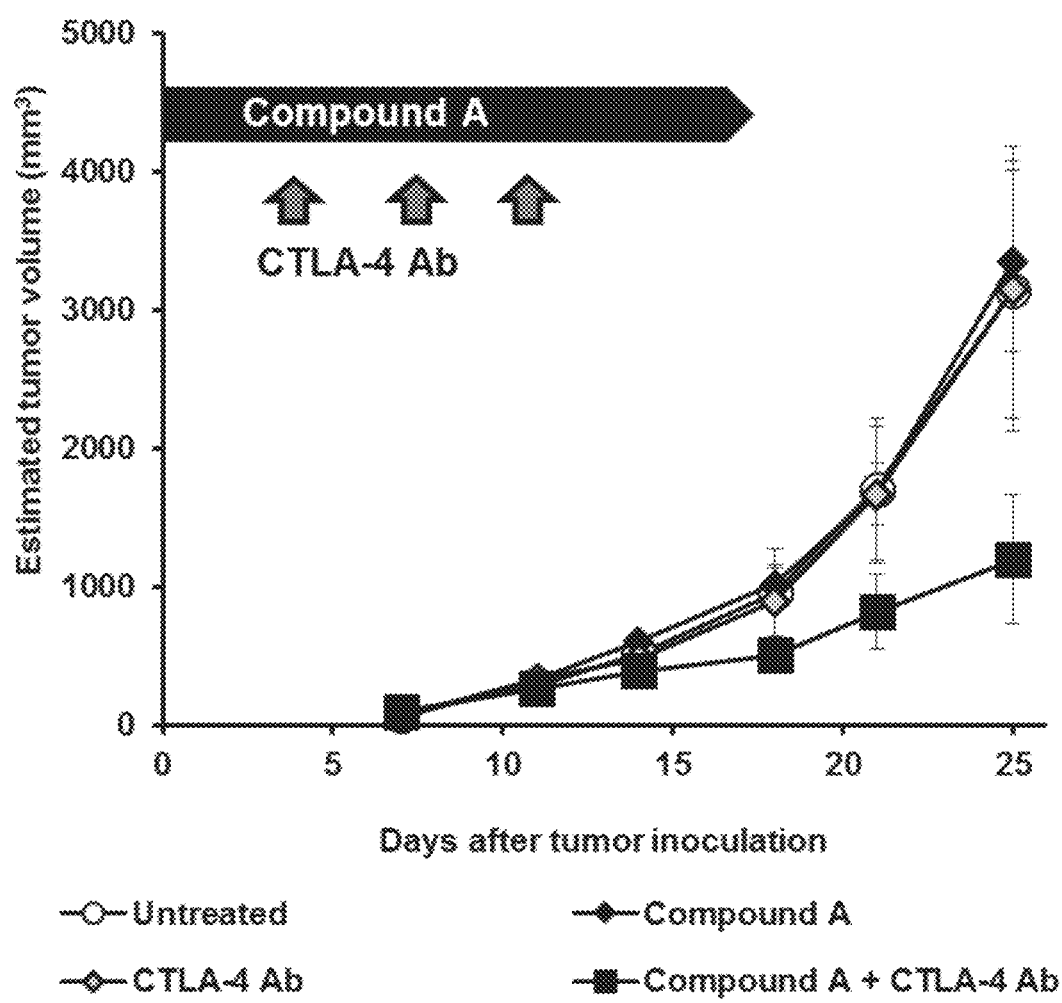

[Figure 7]
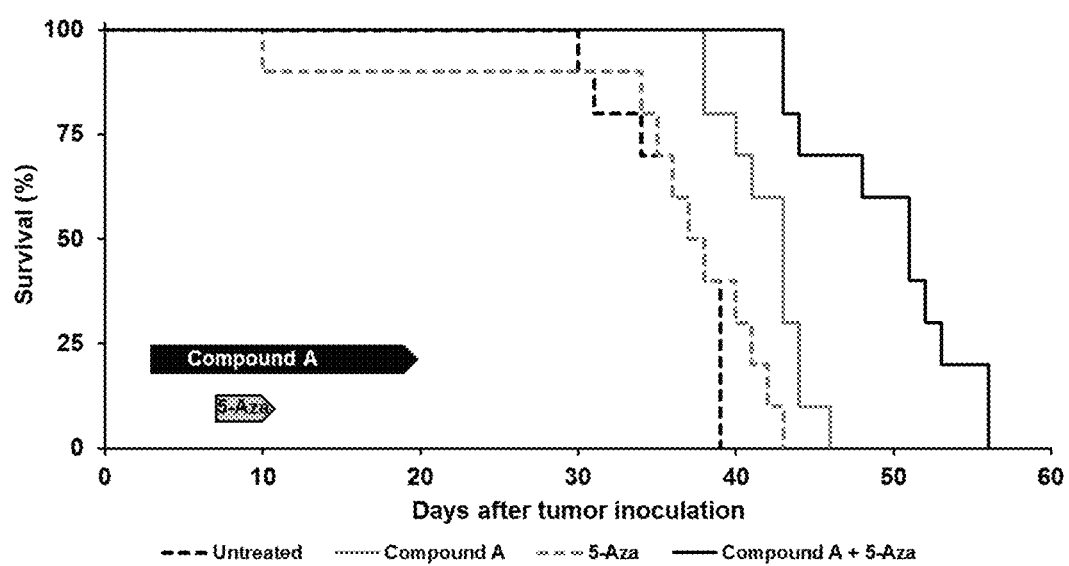

[Figure 8]
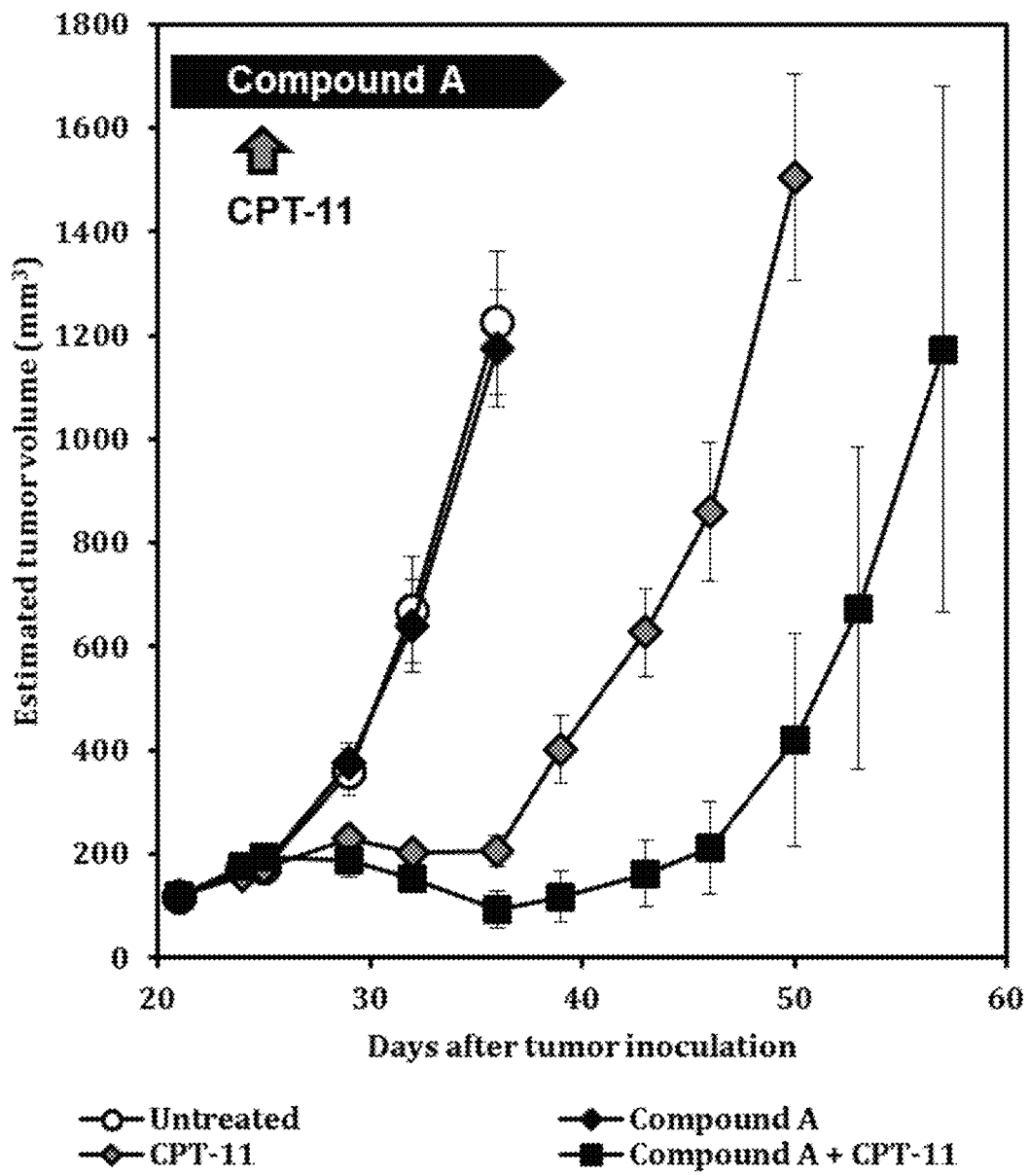

[Figure 9]
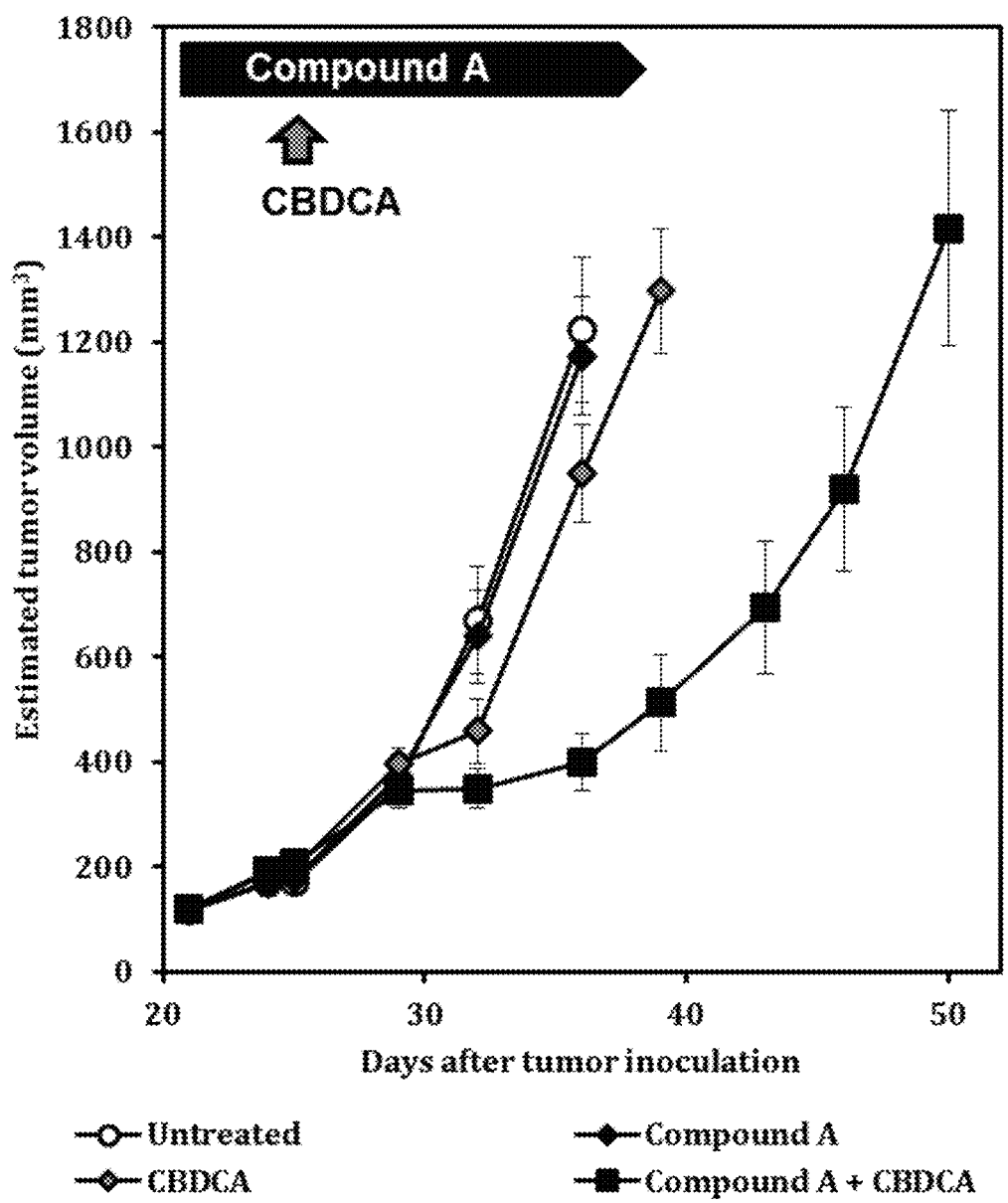

EZH1/2 DUAL INHIBITOR-CONTAINING PHARMACEUTICAL COMPOSITION TO BE USED AS A COMBINATION DRUG

CROSS-REFERENCE TO RELATED APPLICATIONS

The present application claims priority under 35 U.S.C. § 371 to International Patent Application No. PCT/JP2019/046794, filed Nov. 29, 2019, which claims priority to and the benefit of Japanese Patent Application No. 2018-223780, filed on Nov. 29, 2018. The contents of these applications are hereby incorporated by reference in their entireties.

TECHNICAL FIELD

The present invention relates to a combination drug containing an EZH1/2 dual inhibitor and another medical agent in combination and exerting an excellent anticancer effect.

BACKGROUND ART

The polycomb family negatively regulates gene expression through chromatin control mediated by histone modification. Enhancer of zeste homologue 1/2 (EZH1/2) is an active center of polycomb repressive complex 2 (PRC2), which tri-methylates histone H3K27. EZH1 and EZH2 mutually compensate each other's functions and maintain an epigenome within a cell. Inhibition of EZH2 reduces the methylation level at H3K27 of a whole cell; however, the effect is limited by the compensation effect of EZH1. If EZH1 and EZH2 are simultaneously inhibited, methylation is more effectively eliminated (Non Patent Literature 1). Abnormalities of components of PRC2 cause cancer and functional abnormalities of stem cells. Particularly, abnormalities of the EZH2 gene and elevated expression thereof induce accumulation of methylated H3K27me3, which is identified in many cancers. Studies have been aggressively conducted focusing on EZH2 as a new molecular target for cancer (Non Patent Literatures 2, 3).

An EZH1/2 dual inhibitor, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxol-5-carboxamide and a pharmaceutically acceptable salt thereof are known (Patent Literature 1).

In terms of cancer therapy, it is known that therapies using a plurality of anticancer agents in combination are effective, and various studies (on combination therapy) have been actively conducted. However, it is extremely difficult to find a combination of medical agents exerting a combined effect, and a type of cancer on which the effect is exerted. Particularly, with regard to an EZH1/2 dual inhibitor, i.e., (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxol-5-carboxamide and a pharmaceutically acceptable salt thereof, there is no literature reporting combined use thereof with another medical agent. Because of this, the kind of medical agent to be used in combination with this to exert a combined effect has not yet been known.

CITATION LIST

Patent Literature

Patent Literature 1: WO2015141616

Non Patent Literature

Non Patent Literature 1: Shen, X et al., Mol Cell 2008; 32(4): 491-502.
Non Patent Literature 2: Sparmann A, van Lohuizen M., Nat Rev Cancer 2006; 6:846.
Non Patent Literature 3: Lund, Adams, Copland., Leukemia 2014; 28(1): 44-9.

SUMMARY OF INVENTION

Technical Problem

An object of the present invention is to provide a combination drug having an EZH1/2 dual inhibitor in combination with another medical agent and exerting an excellent anticancer effect.

Solution to Problem

The present inventors conducted intensive studies with a view to achieving the object. As a result, they found that an excellent anticancer effect can be exerted by using an EZH1/2 dual inhibitor in combination with at least one second medical agent selected from a metabolic antagonist, an alkylating agent, a platinum preparation, an antitumor antibiotic substance, an antitumor plant component, a hormonal agent, an immunomodulator, a molecular target drug and an immune checkpoint inhibitor. Based on the finding, the present invention was accomplished. The present invention relates to the following (1) to (59).

(1) A pharmaceutical composition for use in treating cancer, wherein a compound represented by the following formula (I):

[Formula 1]

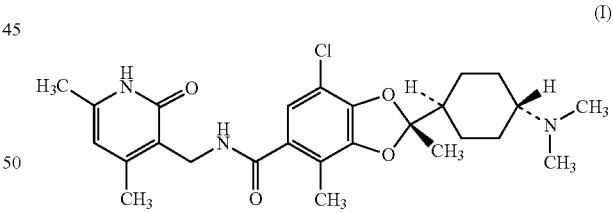

or a pharmaceutically acceptable salt thereof, and at least one second medical agent selected from a metabolic antagonist, an alkylating agent, a platinum preparation, an antitumor antibiotic substance, an antitumor plant component, a hormonal agent, an immunomodulator, a molecular target drug and an immune checkpoint inhibitor are administered in combination.

(2) The pharmaceutical composition according to (1), wherein the compound represented by the above formula (I) or a pharmaceutically acceptable salt thereof and the second medical agent are administered at the same time or different times.

(3) The pharmaceutical composition according to (1) or (2), wherein the compound represented by the above formula (I) or a pharmaceutically acceptable salt thereof is a p-toluenesulfonate salt of the compound represented by the above formula (I).

(4) The pharmaceutical composition according to any one of (1) to (3), wherein the second medical agent is a metabolic antagonist.

(5) The pharmaceutical composition according to any one of (1) to (3), wherein the second medical agent is at least one selected from fluorouracil, decitabine, gemcitabine, azacytidine, cytarabine or a pharmaceutically acceptable salt of any of these medical agents.

(6) The pharmaceutical composition according to any one of (1) to (3), wherein the second medical agent is an alkylating agent.

(7) The pharmaceutical composition according to any one of (1) to (3), wherein the second medical agent is nimustine or a pharmaceutically acceptable salt thereof.

(8) The pharmaceutical composition according to any one of (1) to (3), wherein the second medical agent is a platinum preparation.

(9) The pharmaceutical composition according to any one of (1) to (3), wherein the second medical agent is carboplatin.

(10) The pharmaceutical composition according to any one of (1) to (3), wherein the second medical agent is an antitumor antibiotic substance.

(11) The pharmaceutical composition according to any one of (1) to (3), wherein the second medical agent is doxorubicin or a pharmaceutically acceptable salt thereof.

(12) The pharmaceutical composition according to any one of (1) to (3), wherein the second medical agent is an antitumor plant component.

(13) The pharmaceutical composition according to any one of (1) to (3), wherein the second medical agent is at least one selected from docetaxel, irinotecan, SN-38, vincristine, etoposide or a pharmaceutically acceptable salt of any of these medical agents.

(14) The pharmaceutical composition according to any one of (1) to (3), wherein the second medical agent is a hormonal agent.

(15) The pharmaceutical composition according to any one of (1) to (3), wherein the second medical agent is dexamethasone or a pharmaceutically acceptable salt thereof.

(16) The pharmaceutical composition according to any one of (1) to (3), wherein the second medical agent is an immunomodulator.

(17) The pharmaceutical composition according to any one of (1) to (3), wherein the second medical agent is lenalidomide.

(18) The pharmaceutical composition according to any one of (1) to (3), wherein the second medical agent is a molecular target drug.

(19) The pharmaceutical composition according to any one of (1) to (3), wherein the second medical agent is at least one selected from bortezomib, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 5-{8-[(3R)-4-acetyl-3-methylpiperazin-1-yl]-6-morpholin-4-yl-9-(2,2,2-trifluoroethyl)-9H-purin-2-yl}pyrimidin-2-amine, erlotinib, lapatinib, olaparib, vorinostat, SAHA, sorafenib, milademetan, quizartinib, venetoclax, BDM, ibrutinib, lenalidomide, panobinostat, rituximab or a pharmaceutically acceptable salt of any of these medical agents.

(20) The pharmaceutical composition according to any one of (1) to (3), wherein the second medical agent is an immune checkpoint inhibitor.

(21) The pharmaceutical composition according to any one of (1) to (3), wherein the second medical agent is at least one selected from an anti-PD-1 antibody, an anti-PD-L1 antibody or an anti-CLTA-4 antibody.

(22) The pharmaceutical composition according to any one of (1) to (3), wherein the second medical agent is at least one selected from nivolumab, pembrolizumab, avelumab, atezolizumab, durvalumab or ipilimumab.

(23) A pharmaceutical composition for use in treating cancer, wherein a medical agent containing a compound represented by the above formula (I) or a pharmaceutically acceptable salt thereof, and medical agents involved in CHOP therapy are administered in combination.

(24) A pharmaceutical composition for use in treating cancer, wherein a medical agent containing a compound represented by the above formula (I) or a pharmaceutically acceptable salt thereof, and medical agents involved in R-CHOP therapy are administered in combination.

(25) The pharmaceutical composition according to any one of (1) to (24), wherein the cancer is hematological cancer.

(26) The pharmaceutical composition according to (25), wherein the hematological cancer is non-Hodgkin's lymphoma.

(27) The pharmaceutical composition according to (25), wherein the hematological cancer is acute myelogenous leukemia.

(28) The pharmaceutical composition according to (25), wherein the hematological cancer is multiple myeloma.

(29) The pharmaceutical composition according to any one of (1) to (24), wherein the cancer is a solid cancer.

(30) A compound represented by the following formula (I) or a pharmaceutically acceptable salt thereof, administered in combination with at least one second medical agent selected from a metabolic antagonist, an alkylating agent, a platinum preparation, an antitumor antibiotic substance, an antitumor plant component, a hormonal agent, an immunomodulator, a molecular target drug and an immune checkpoint inhibitor.

[Formula 2]

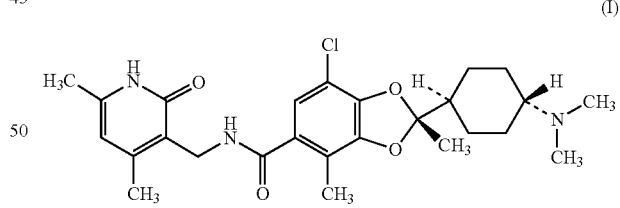

(I)

(31) The compound or a pharmaceutically acceptable salt thereof according to (30), wherein the compound or a pharmaceutically acceptable salt thereof is administered with the second medical agent at the same time or different times.

(32) The compound or a pharmaceutically acceptable salt thereof according to (30) or (31), wherein the compound represented by the above formula (I) or a pharmaceutically acceptable salt thereof is a p-toluenesulfonate salt of the compound represented by the above formula (I).

(33) The compound or a pharmaceutically acceptable salt thereof according to any one of (30) to (32), wherein the second medical agent is a metabolic antagonist.

(34) The compound or a pharmaceutically acceptable salt thereof according to any one of (30) to (32), wherein the second medical agent is at least one selected from fluorouracil, decitabine, gemcitabine, azacytidine, cytarabine or a pharmaceutically acceptable salt of any of these medical agents.

(35) The compound or a pharmaceutically acceptable salt thereof according to any one of (30) to (32), wherein the second medical agent is an alkylating agent.

(36) The compound or a pharmaceutically acceptable salt thereof according to any one of (30) to (32), wherein the second medical agent is nimustine or a pharmaceutically acceptable salt thereof.

(37) The compound or a pharmaceutically acceptable salt thereof according to any one of (30) to (32), wherein the second medical agent is a platinum preparation.

(38) The compound or a pharmaceutically acceptable salt thereof according to any one of (30) to (32), wherein the second medical agent is carboplatin.

(39) The compound or a pharmaceutically acceptable salt thereof according to any one of (30) to (32), wherein the second medical agent is an antitumor antibiotic substance.

(40) The compound or a pharmaceutically acceptable salt thereof according to any one of (30) to (32), wherein the second medical agent is doxorubicin or a pharmaceutically acceptable salt thereof.

(41) The compound or a pharmaceutically acceptable salt thereof according to any one of (30) to (32), wherein the second medical agent is an antitumor plant component.

(42) The compound or a pharmaceutically acceptable salt thereof according to any one of (30) to (32), wherein the second medical agent is at least one selected from docetaxel, irinotecan, SN-38, vincristine, etoposide or a pharmaceutically acceptable salt of any of these medical agents.

(43) The compound or a pharmaceutically acceptable salt thereof according to any one of (30) to (32), wherein the second medical agent is a hormonal agent.

(44) The compound or a pharmaceutically acceptable salt thereof according to any one of (30) to (32), wherein the second medical agent is dexamethasone or a pharmaceutically acceptable salt thereof.

(45) The compound or a pharmaceutically acceptable salt thereof according to any one of (30) to (32), wherein the second medical agent is an immunomodulator.

(46) The compound or a pharmaceutically acceptable salt thereof according to any one of (30) to (32), wherein the second medical agent is lenalidomide.

(47) The compound or a pharmaceutically acceptable salt thereof according to any one of (30) to (32), wherein the second medical agent is a molecular target drug.

(48) The compound or a pharmaceutically acceptable salt thereof according to any one of (30) to (32), wherein the second medical agent is at least one selected from bortezomib, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 5-{8-[(3R)-4-acetyl-3-methylpiperazin-1-yl]-6-morpholin-4-yl-9-(2,2,2-trifluoroethyl)-9H-purin-2-yl}pyrimidin-2-amine, erlotinib, lapatinib, olaparib, vorinostat, SAHA, sorafenib, milademetan, quizartinib, venetoclax, BDM, ibrutinib, lenalidomide, panobinostat, rituximab or a pharmaceutically acceptable salt of any of these medical agents.

(49) The pharmaceutical composition according to any one of (30) to (32), wherein the second medical agent is an immune checkpoint inhibitor.

(50) The pharmaceutical composition according to any one of (30) to (32), wherein the second medical agent is at least one selected from an anti-PD-1 antibody, an anti-PD-L1 antibody or an anti-CLTA-4 antibody.

(51) The pharmaceutical composition according to any one of (30) to (32), wherein the second medical agent is at least one selected from nivolumab, pembrolizumab, avelumab, atezolizumab, durvalumab or ipilimumab.

(52) A compound represented by the above formula (I) or a pharmaceutically acceptable salt thereof, administered in combination with medical agents involved in CHOP therapy.

(53) A compound represented by the above formula (I) or a pharmaceutically acceptable salt thereof, administered in combination with medical agents involved in R-CHOP therapy.

(54) The compound or a pharmaceutically acceptable salt thereof according to any one of (30) to (53), for use in treating cancer.

(55) The compound or a pharmaceutically acceptable salt thereof according to (54), wherein the cancer is hematological cancer.

(56) The pharmaceutical composition according to (55), wherein the hematological cancer is non-Hodgkin's lymphoma.

(57) The pharmaceutical composition according to (55), wherein the hematological cancer is acute myelogenous leukemia.

(58) The pharmaceutical composition according to (55), wherein the hematological cancer is multiple myeloma.

(59) The pharmaceutical composition according to (54), wherein the cancer is a solid cancer.

Another embodiment of the present invention relates to the following (1) to (51).

(1) A pharmaceutical composition for use in treating cancer, wherein a compound represented by the following formula (I):

[Formula 3]

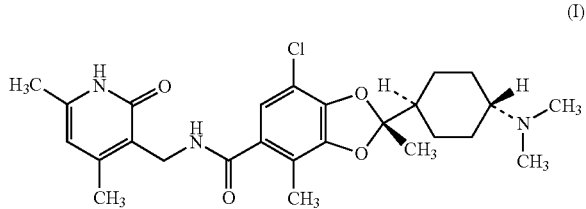

or a pharmaceutically acceptable salt thereof, and at least one second medical agent selected from a metabolic antagonist, an alkylating agent, a platinum preparation, an antitumor antibiotic substance, an antitumor plant component, a hormonal agent, an immunomodulator and a molecular target drug are administered in combination.

(2) The pharmaceutical composition according to (1), wherein the compound represented by the above formula (I) or a pharmaceutically acceptable salt thereof and the second medical agent are administered at the same time or different times.

(3) The pharmaceutical composition according to (1) or (2), wherein the compound represented by the above formula (I) or a pharmaceutically acceptable salt thereof is a p-toluenesulfonate salt of the compound represented by the above formula (I).

(4) The pharmaceutical composition according to any one of (1) to (3), wherein the second medical agent is a metabolic antagonist.

(5) The pharmaceutical composition according to any one of (1) to (3), wherein the second medical agent is at least one selected from fluorouracil, decitabine, gemcitabine, azacytidine, cytarabine or a pharmaceutically acceptable salt of any of these medical agents.

(6) The pharmaceutical composition according to any one of (1) to (3), wherein the second medical agent is an alkylating agent.

(7) The pharmaceutical composition according to any one of (1) to (3), wherein the second medical agent is nimustine or a pharmaceutically acceptable salt thereof.

(8) The pharmaceutical composition according to any one of (1) to (3), wherein the second medical agent is a platinum preparation.

(9) The pharmaceutical composition according to any one of (1) to (3), wherein the second medical agent is carboplatin.

(10) The pharmaceutical composition according to any one of (1) to (3), wherein the second medical agent is an antitumor antibiotic substance.

(11) The pharmaceutical composition according to any one of (1) to (3), wherein the second medical agent is doxorubicin or a pharmaceutically acceptable salt thereof.

(12) The pharmaceutical composition according to any one of (1) to (3), wherein the second medical agent is an antitumor plant component.

(13) The pharmaceutical composition according to any one of (1) to (3), wherein the second medical agent is at least one selected from docetaxel, irinotecan, SN-38, vincristine, etoposide or a pharmaceutically acceptable salt of any of these medical agents.

(14) The pharmaceutical composition according to any one of (1) to (3), wherein the second medical agent is a hormonal agent.

(15) The pharmaceutical composition according to any one of (1) to (3), wherein the second medical agent is dexamethasone or a pharmaceutically acceptable salt thereof.

(16) The pharmaceutical composition according to any one of (1) to (3), wherein the second medical agent is an immunomodulator.

(17) The pharmaceutical composition according to any one of (1) to (3), wherein the second medical agent is lenalidomide.

(18) The pharmaceutical composition according to any one of (1) to (3), wherein the second medical agent is a molecular target drug.

(19) The pharmaceutical composition according to any one of (1) to (3), wherein the second medical agent is at least one selected from bortezomib, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 5-{8-[(3R)-4-acetyl-3-methylpiperazin-1-yl]-6-morpholin-4-yl-9-(2,2,2-trifluoroethyl)-9H-purin-2-yl}pyrimidin-2-amine, erlotinib, lapatinib, olaparib, vorinostat, SAHA, sorafenib, milademetan, quizartinib, venetoclax, BDM, ibrutinib, lenalidomide, panobinostat or a pharmaceutically acceptable salt of any of these medical agents.

(20) A pharmaceutical composition for use in treating cancer, wherein a medical agent containing a compound represented by the above formula (I) or a pharmaceutically acceptable salt thereof, and medical agents involved in CHOP therapy are administered in combination.

(21) The pharmaceutical composition according to any one of (1) to (20), wherein the cancer is hematological cancer.

(22) The pharmaceutical composition according to (21), wherein the hematological cancer is non-Hodgkin's lymphoma.

(23) The pharmaceutical composition according to (21), wherein the hematological cancer is acute myelogenous leukemia.

(24) The pharmaceutical composition according to (21), wherein the hematological cancer is multiple myeloma.

(25) The pharmaceutical composition according to any one of (1) to (20), wherein the cancer is a solid cancer.

(26) A compound represented by the following formula (I) or a pharmaceutically acceptable salt thereof, administered in combination with at least one second medical agent selected from a metabolic antagonist, an alkylating agent, a platinum preparation, an antitumor antibiotic substance, an antitumor plant component, a hormonal agent, an immunomodulator and a molecular target drug.

[Formula 4]

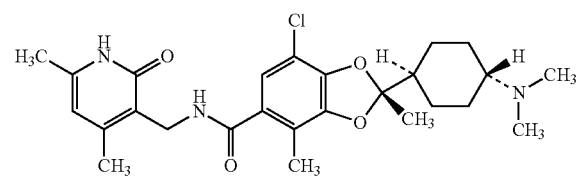

(I)

(27) The compound or a pharmaceutically acceptable salt thereof according to (26), wherein the compound or a pharmaceutically acceptable salt thereof is administered with the second medical agent at the same time or different times.

(28) The compound or a pharmaceutically acceptable salt thereof according to (26) or (27), wherein the compound represented by the above formula (I) or a pharmaceutically acceptable salt thereof is a p-toluenesulfonate salt of the compound represented by the above formula (I).

(29) The compound or a pharmaceutically acceptable salt thereof according to any one of (26) to (28), wherein the second medical agent is a metabolic antagonist.

(30) The compound or a pharmaceutically acceptable salt thereof according to any one of (26) to (28), wherein the second medical agent is at least one selected from fluorouracil, decitabine, gemcitabine, azacytidine, cytarabine or a pharmaceutically acceptable salt of any of these medical agents.

(31) The compound or a pharmaceutically acceptable salt thereof according to any one of (26) to (28), wherein the second medical agent is an alkylating agent.

(32) The compound or a pharmaceutically acceptable salt thereof according to any one of (26) to (28), wherein the second medical agent is nimustine or a pharmaceutically acceptable salt thereof.

(33) The compound or a pharmaceutically acceptable salt thereof according to any one of (26) to (28), wherein the second medical agent is a platinum preparation.

(34) The compound or a pharmaceutically acceptable salt thereof according to any one of (26) to (28), wherein the second medical agent is carboplatin.

(35) The compound or a pharmaceutically acceptable salt thereof according to any one of (26) to (28), wherein the second medical agent is an antitumor antibiotic substance.

(36) The compound or a pharmaceutically acceptable salt thereof according to any one of (26) to (28), wherein the second medical agent is doxorubicin or a pharmaceutically acceptable salt thereof.

(37) The compound or a pharmaceutically acceptable salt thereof according to any one of (26) to (28), wherein the second medical agent is an antitumor plant component.

(38) The compound or a pharmaceutically acceptable salt thereof according to any one of (26) to (28), wherein the second medical agent is at least one selected from docetaxel, irinotecan, SN-38, vincristine, etoposide or a pharmaceutically acceptable salt of any of these medical agents.

(39) The compound or a pharmaceutically acceptable salt thereof according to any one of (26) to (28), wherein the second medical agent is a hormonal agent.

(40) The compound or a pharmaceutically acceptable salt thereof according to any one of (26) to (28), wherein the second medical agent is dexamethasone or a pharmaceutically acceptable salt thereof.

(41) The compound or a pharmaceutically acceptable salt thereof according to any one of (26) to (28), wherein the second medical agent is an immunomodulator.

(42) The compound or a pharmaceutically acceptable salt thereof according to any one of (26) to (28), wherein the second medical agent is lenalidomide.

(43) The compound or a pharmaceutically acceptable salt thereof according to any one of (26) to (28), wherein the second medical agent is a molecular target drug.

(44) The compound or a pharmaceutically acceptable salt thereof according to any one of (26) to (28), wherein the second medical agent is at least one selected from bortezomib, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 5-{8-[(3R)-4-acetyl-3-methylpiperazin-1-yl]-6-morpholin-4-yl-9-(2,2,2-trifluoroethyl)-9H-purin-2-yl}pyrimidin-2-amine, erlotinib, lapatinib, olaparib, vorinostat, SAHA, sorafenib, milademetan, quizartinib, venetoclax, BDM, ibrutinib, panobinostat or a pharmaceutically acceptable salt of any of these medical agents.

(45) A compound represented by the above formula (I) or a pharmaceutically acceptable salt thereof, administered in combination with medical agents involved in CHOP therapy.

(46) The compound or a pharmaceutically acceptable salt thereof according to any one of (26) to (45) for use in treating cancer.

(47) The compound or a pharmaceutically acceptable salt thereof according to (46), wherein the cancer is hematological cancer.

(48) The pharmaceutical composition according to (47), wherein the hematological cancer is non-Hodgkin's lymphoma.

(49) The pharmaceutical composition according to (47), wherein the hematological cancer is acute myelogenous leukemia.

(50) The pharmaceutical composition according to (47), wherein the hematological cancer is multiple myeloma.

(51) The pharmaceutical composition according to (46), wherein the cancer is a solid cancer.

Advantageous Effects of Invention

Owing to the present invention, an excellent anticancer effect can be exerted by using an EZH1/2 dual inhibitor in combination with at least one second medical agent selected from a metabolic antagonist, an alkylating agent, a platinum preparation, an antitumor antibiotic substance, an antitumor plant component, a hormonal agent, an immunomodulator, a molecular target drug and an immune checkpoint inhibitor.

BRIEF DESCRIPTION OF DRAWINGS

FIG. 1 shows an evaluation of the combined effect of Compound A and CHOP therapy on the KARPAS-422 xenograft model. The vertical axis represents tumor volume and the horizontal axis represents the number of days elapsed.

FIG. 2 shows an evaluation of the combined effect of Compound A and R-CHOP therapy on the KARPAS-422 xenograft model. The vertical axis represents tumor volume and the horizontal axis represents the number of days elapsed.

FIG. 3 shows an evaluation of the combined effect of Compound A and rituximab on the WSU-DLCL2 xenograft model. The vertical axis represents tumor volume and the horizontal axis represents the number of days elapsed.

FIG. 4 shows an evaluation of the combined effect of Compound A and an anti-PD-1 antibody on the A20 syngeneic model. The vertical axis represents survival rate and the horizontal axis represents the number of days elapsed.

FIG. 5 shows an evaluation of the combined effect of Compound A and an anti-PD-L1 antibody on the A20 syngeneic model. The vertical axis represents survival rate and the horizontal axis represents the number of days elapsed.

FIG. 6 shows an evaluation of the combined effect of Compound A and an anti-CTLA-4 antibody on the A20 syngeneic model. The vertical axis represents survival rate and the horizontal axis represents the number of days elapsed.

FIG. 7 shows an evaluation of the combined effect of Compound A and 5-azacytidine on the MV-4-11 xenograft model. The vertical axis represents survival rate and the horizontal axis represents the number of days elapsed.

FIG. 8 shows an evaluation of the combined effect of Compound A and irinotecan on the NCI-H446 xenograft model. The vertical axis represents tumor volume, and the horizontal axis represents the number of days elapsed.

FIG. 9 shows an evaluation of the combined effect of Compound A and carboplatin on the NCI-H446 xenograft model. The vertical axis represents tumor volume, and the horizontal axis represents the number of days elapsed.

The compound represented by the formula (I) of the present invention is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxol-5-carboxamide, also known as valemetostat. The compound represented by the formula (I) can be produced, for example, in accordance with a method described in Example 35 of WO2015141616. The whole content of WO2015141616 is incorporated herein by reference.

A pharmaceutically acceptable salt of the compound represented by the formula (I) of the present invention is most preferably (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxol-5-carboxamide p-toluenesulfonate (hereinafter referred to as "Compound A").

In the present invention, the "metabolic antagonist" refers to a medical agent exerting an anticancer effect by inhibiting biosynthesis of a nucleic acid to prevent tumor cells from growing and dividing. Examples of the metabolic antagonist include fluorouracil (also referred to as 5-FU), mercaptopurine, decitabine, gemcitabine (also referred to as GEM), azacytidine (also referred to as 5-Aza), cytarabine (also referred to as Ara-C), methotrexate, tegafur, UFT, S-1, carmofur, doxifluridine, capecitabine and pharmaceutically acceptable salts of these medical agents. Also, prodrugs of the above medical agents, which are converted into the medical agents in vivo, are also included in the metabolic antagonist of the present invention.

In the present invention, a preferable metabolic antagonist is fluorouracil, decitabine, gemcitabine, azacytidine, cytarabine or a pharmaceutically acceptable salt of any of these medical agents. More preferable metabolic antagonist is azacytidine, cytarabine or a pharmaceutically acceptable salt of any of these medical agents.

In the present invention, the "alkylating agent" refers to a medical agent exerting an anticancer effect by alkylating DNA of a cancer cell to prevent cells from proliferating. Examples of the alkylating agent include cyclophosphamide, ifosfamide, dacarbazine, temozolomide, nimustine (also referred to as ACNU), busulfan, procarbazine, melphalan, ranimustine or pharmaceutically acceptable salts of these medical agents. Also, prodrugs of the above medical agents, which are converted into the medical agents in vivo, are also included in the alkylating agent of the present invention. In the present invention, a preferable alkylating agent is nimustine or a pharmaceutically acceptable salt thereof.

In the present invention, the "platinum preparation" refers to a medical agent exerting an anticancer effect by binding DNA of a cancer cell and a platinum atom to inhibit replication of DNA. Examples of the platinum preparation include cisplatin, carboplatin (also referred to as CBDCA) and oxaliplatin. In the present invention, a preferable platinum preparation is carboplatin.

In the present invention, the "antitumor antibiotic substance" refers to a medical agent exerting an anticancer effect by inhibiting DNA synthesis of a cancer cell, cutting a DNA chain and inhibiting topoisomerase II. Examples of the antitumor antibiotic substance include doxorubicin (also referred to as DOX), daunorubicin, epirubicin, aclarubicin, idarubicin, pirarubicin, amrubicin, bleomycin, mitomycin C and pharmaceutically acceptable salts of these medical agents. In the present invention, a preferable antitumor antibiotic substance is doxorubicin or a pharmaceutically acceptable salt thereof.

In the present invention, the "antitumor plant component" refers to an antitumor alkaloid or a derivative thereof. Examples of the antitumor plant component include vinblastine, vincristine (also referred to as VCR), paclitaxel, docetaxel (also referred to as DTX), irinotecan (also referred to as CPT-11), SN-38, etoposide (also referred to as ETP) and pharmaceutically acceptable salts of these medical agents. Prodrugs of the above medical agents, which are converted into the medical agents in vivo, are also included in the antitumor plant component of the present invention.

In the present invention, a preferable antitumor plant component is docetaxel, SN-38, irinotecan, vincristine, etoposide or a pharmaceutically acceptable salt of any of these medical agents. More preferable antitumor plant components are SN-38, irinotecan, vincristine, etoposide or a pharmaceutically acceptable salt of any of these medical agents.

In the present invention, the "hormonal agent" refers to a medical agent exerting an anticancer effect by suppressing secretion and action of a predetermined hormone. Examples of the hormonal agent include hydrocortisone, cortisone, prednisolone, methylprednisolone, triamcinolone, paramethasone, betamethasone, dexamethasone and pharmaceutically acceptable salts of these medical agents. Prodrugs of the above medical agents, which are converted into the medical agents in vivo, are also included in the hormonal agent of the present invention. In the present invention, a preferable hormonal agent includes dexamethasone and a pharmaceutically acceptable salt thereof.

In the present invention, the "immunomodulator" refers to a medical agent exerting an anticancer effect by regulating actions of the immune system. Examples of the immunomodulator include thalidomide and lenalidomide (also referred to as LEN). In the present invention, a preferable immunomodulator is lenalidomide.

In the present invention, the "molecular target drug" refers to a medical agent exerting an anticancer effect by acting on a predetermined molecule of a cancer cell. Molecular target drugs are classified based on mechanism of action. Examples of the molecular target drug that can be used in the present invention include a proteasome inhibitor, an EGFR inhibitor, an EGFR/HER2 dual inhibitor, a PARP inhibitor, a HDAC inhibitor, a multikinase inhibitor, an FLT3 inhibitor, a BCL-2 inhibitor, a myosin II inhibitor, a BTK inhibitor, a DAC inhibitor, a BRD4 inhibitor, an mTOR inhibitor, a PI3K/mTOR dual inhibitor, an MDM2 inhibitor and various antibodies. Specific examples of the medical agent include bortezomib, erlotinib, lapatinib, olaparib, vorinostat (also referred to as SAHA), sorafenib, quizartinib, venetoclax (also referred to as VEN), ibrutinib (also referred to as IBR), panobinostat, rituximab, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 5-{8-[(3R)-4-acetyl-3-methylpiperazin-1-yl]-6-morpholin-4-yl-9-(2,2,2-trifluoroethyl)-9H-purin-2-yl}pyrimidin-2-amine, milademetan and pharmaceutically acceptable salts of these medical agents.

In the present invention, "1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one" is an mTOR inhibitor, which can be produced, for example, in accordance with a method disclosed in Example 42 of WO2010016490. The whole content of WO2010016490 is incorporated herein by reference.

In the present invention, "5-{8-[(3R)-4-acetyl-3-methylpiperazin-1-yl]-6-morpholin-4-yl-9-(2,2,2-trifluoroethyl)-9H-purin-2-yl}pyrimidin-2-amine" is a PI3K/mTOR dual inhibitor, which can be produced, for example, in accordance with a method disclosed in Example 59 of WO2010044401. The whole content of WO2010044401 is incorporated herein by reference.

In the present invention, "Milademetan" is an MDM2 inhibitor, which can be produced, for example, in accordance with a method disclosed in Example 70 of WO2012121361. The whole content of WO2012121361 is incorporated herein by reference.

In the present invention, the "immune checkpoint inhibitor" refers to a medical agent exerting an anticancer effect by blocking the immunosuppressive escape mechanism by an immune checkpoint molecule to proliferate and activate T cells. Examples of the immune checkpoint inhibitor that can be used in the present invention include an anti-PD-1 antibody, an anti-PD-L1 antibody and an anti-CTLA-4 antibody. Specific examples of the medical agent include nivolumab, pembrolizumab, avelumab, atezolizumab, durvalumab and ipilimumab.

In the present invention, "CHOP therapy" refers to a chemotherapy for cancer, by administering cyclophosphamide, doxorubicin, vincristine and prednisolone in combination. The medical agents involved in CHOP therapy refer to these four medical agents. It is used for treating, for example, malignant lymphoma.

In the present invention, "R-CHOP therapy" refers to a chemotherapy for cancer, by administering rituximab, cyclophosphamide, doxorubicin, vincristine and prednisolone in combination. The medical agents involved in R-CHOP therapy refer to these five medical agents. It is used for treating, for example, malignant lymphoma.

It is suggested that EZH1 and/or EZH2 are involved in, e.g., proliferation of cancer and survival. Because of this, the present invention is preferably used for cancer in which the expression levels of EZH1 and/or EZH2 are increased and/or cancer having a mutation(s) in EZH1 and/or EZH2.

Whether the expression levels of EZH1 and/or EZH2 are increased or not can be determined by analyzing, e.g., the expression levels of EZH1 and/or EZH2 in a test tissue (collected by, for example, blood sampling or biopsy) of a patient by e.g., western blot, ELISA, northern blot, quantitative PCR, DNA tip tissue immunostaining and/or a commonly known method using pathological techniques.

Whether or not a mutation is present in EZH1 and/or EZH2 can be determined by examining the nucleotide sequence of genomic DNA.

In the present invention, "cancer" refers to a whole group of malignant tumors.

Cancer can be classified into "solid cancer" and "hematological cancer". Solid cancer can be classified into "epithelial cell cancer" and "non-epithelial cell cancer". Epithelial cell cancer is derived from epithelial cells. Examples thereof include lung cancer, gastric cancer, liver cancer, kidney cancer, prostate cancer, pancreatic cancer, colorectal cancer, breast cancer and ovarian cancer. Non-epithelial cell cancer is derived from non-epithelial cells such as bone and muscle. Examples thereof include osteosarcoma, chondrosarcoma and rhabdomyosarcoma. Hematological cancer is derived from a hematopoietic organ and can be classified into, e.g., malignant lymphoma, leukemia and multiple myeloma. In hematological cancer, a pathological condition, which is sometimes classified into a precancerous stage, such as myelodysplastic syndrome, is also included.

Malignant lymphoma can be classified into, for example, Hodgkin's lymphoma and non-Hodgkin's lymphoma. Examples of the non-Hodgkin's lymphoma include mantle cell lymphoma (also referred to as MCL), diffuse large B-cell lymphoma, (also referred to as DLBCL), adult T-cell leukemia/lymphoma (also referred to as ATLL) and peripheral T-cell lymphoma (also referred to as PTCL).

Leukemia is classified into, for example, acute myelogenous leukemia (also referred to as AML), chronic myelogenous leukemia (also referred to as CML), acute lymphoid leukemia (also referred to as ALL), chronic lymphoid leukemia (also referred to as CLL), and myelodysplastic syndromes (also referred to as MDS).

The type of cancer to be treated by the present invention is not particularly limited as long as it is susceptible to the combination therapy of the present invention. For example, a hematological cancer such as leukemia, malignant lymphoma, multiple myeloma or myelodysplastic syndrome; brain tumor, head and neck cancer, esophageal cancer, gastric cancer, appendix cancer, colorectal cancer, anal cancer, gallbladder cancer, bile duct cancer, pancreatic cancer, gastrointestinal stromal tumor, lung cancer, liver cancer, mesothelioma, thyroid cancer, kidney cancer, prostate cancer, neuroendocrine tumor, melanoma, breast cancer, endometrial cancer, cervical cancer, ovarian cancer, osteosarcoma, soft tissue sarcoma, Kaposi's sarcoma, myoma, kidney cancer, bladder cancer or testicular cancer can be mentioned.

The hematological cancer to be treated by the present invention preferably includes leukemia, malignant lymphoma, multiple myeloma and myelodysplastic syndrome, and particularly preferably, acute myelogenous leukemia, non-Hodgkin's lymphoma and multiple myeloma.

The non-Hodgkin's lymphoma to be treated by the present invention preferably includes mantle cell lymphoma, diffuse large B-cell lymphoma, adult T cell leukemia/lymphoma and peripheral T cellular lymphoma.

The solid cancer to be treated by the present invention preferably includes lung cancer, gastric cancer and colorectal cancer.

In the present invention, a combination of a medical agent containing the compound represented by the formula (I) or a pharmaceutically acceptable salt thereof and a medical agent containing fluorouracil or a pharmaceutically acceptable salt thereof, can be used for, e.g., gastric cancer, liver cancer, colon/rectal cancer, small intestine cancer, colorectal cancer, breast cancer, pancreatic cancer, cervical cancer, endometrial cancer, ovarian cancer, esophageal cancer, lung cancer and head and neck cancer.

In the present invention, a combination of a medical agent containing the compound represented by the formula (I) or a pharmaceutically acceptable salt thereof and a medical agent containing gemcitabine or a pharmaceutically acceptable salt thereof, can be used for, e.g., lung cancer, pancreatic cancer, biliary tract cancer, urothelial cancer, breast cancer, ovarian cancer and malignant lymphoma.

In the present invention, a combination of a medical agent containing the compound represented by the formula (I) or a pharmaceutically acceptable salt thereof and a medical agent containing azacytidine or a pharmaceutically acceptable salt thereof, can be used for, e.g., myelodysplastic syndrome.

In the present invention, a combination of a medical agent containing the compound represented by the formula (I) or a pharmaceutically acceptable salt thereof and a medical agent containing cytarabine or a pharmaceutically acceptable salt thereof, can be used for, e.g., acute myelogenous leukemia, gastric cancer, pancreatic cancer, liver cancer, colon cancer, lung cancer, breast cancer, cervical cancer, endometrial cancer, ovarian cancer, bladder cancer and malignant lymphoma.

In the present invention, a combination of a medical agent containing the compound represented by the formula (I) or a pharmaceutically acceptable salt thereof and a medical agent containing nimustine or a pharmaceutically acceptable salt thereof, can be used for, e.g., brain tumor, gastric cancer, liver cancer, colorectal cancer, lung cancer, malignant lymphoma and leukemia.

In the present invention, a combination of a medical agent containing the compound represented by the formula (I) or a pharmaceutically acceptable salt thereof and a medical agent containing carboplatin or a pharmaceutically acceptable salt thereof, can be used for, e.g., head and neck cancer, lung cancer, breast cancer, ovarian cancer, cervical cancer, malignant lymphoma and pediatric cancer.

In the present invention, a combination of a medical agent containing the compound represented by the formula (I) or a pharmaceutically acceptable salt thereof and a medical agent containing doxorubicin or a pharmaceutically acceptable salt thereof, can be used for hematological cancers. Of the hematological cancers, malignant lymphomas are preferred as cancers to which the combination is applied. Of the malignant lymphomas, non-Hodgkin's lymphoma is preferred as a malignant lymphoma to which the combination is applied.

In another aspect, the combination can be used for solid cancers such as lung cancer, gastric cancer, pancreatic cancer, colorectal cancer, osteosarcoma, breast cancer and pediatric cancer.

In the present invention, a combination of a medical agent containing the compound represented by the formula (I) or a pharmaceutically acceptable salt thereof and a medical agent containing docetaxel or a pharmaceutically acceptable salt thereof, can be used for, e.g., breast cancer, lung cancer, gastric cancer, head and neck cancer, ovarian cancer, esophageal cancer, endometrial cancer and prostate cancer.

In the present invention, a combination of a medical agent containing the compound represented by the formula (I) or a pharmaceutically acceptable salt thereof and a medical agent containing SN-38 or a pharmaceutically acceptable salt thereof, can be used for, e.g., lung cancer, cervical cancer, ovarian cancer, gastric cancer, colorectal cancer, breast cancer, skin cancer (including, for example, squamous cell cancer), malignant lymphoma, pancreatic cancer and pediatric cancer.

In the present invention, a combination of a medical agent containing the compound represented by the formula (I) or a pharmaceutically acceptable salt thereof and a medical agent containing etoposide or a pharmaceutically acceptable salt thereof, can be used for hematological cancers. Of the hematological cancers, malignant lymphomas are preferred as hematological cancers to which the combination is applied. Of the malignant lymphomas, non-Hodgkin's lymphoma is preferred as a malignant lymphoma to which the combination is applied.

In another aspect, the combination can be used for solid cancers such as lung cancer, gastric cancer, pancreatic cancer, colorectal cancer, osteosarcoma, breast cancer and pediatric cancer.

In the present invention, a combination of a medical agent containing the compound represented by the formula (I) or a pharmaceutically acceptable salt thereof and a medical agent containing irinotecan or a pharmaceutically acceptable salt thereof, can be used for, e.g., lung cancer, cervical cancer, ovarian cancer, gastric cancer, colorectal cancer, breast cancer, skin cancer (including, for example, squamous cell cancer), malignant lymphoma, pancreatic cancer and pediatric cancer.

In the present invention, a combination of a medical agent containing the compound represented by the formula (I) or a pharmaceutically acceptable salt thereof and a medical agent containing vincristine or a pharmaceutically acceptable salt thereof, can be used for hematological cancers. Of the hematological cancers, malignant lymphomas are preferred hematological cancers to which the combination is applied. Of the malignant lymphomas, non-Hodgkin's lymphoma is preferred as a malignant lymphoma to which the combination is applied.

In another aspect, the combination can be used for solid cancers such as lung cancer, gastric cancer, pancreatic cancer, colorectal cancer, osteosarcoma, breast cancer and pediatric cancer.

In the present invention, a combination of a medical agent containing the compound represented by the formula (I) or a pharmaceutically acceptable salt thereof and a medical agent containing dexamethasone or a pharmaceutically acceptable salt thereof, can be used for e.g., leukemia, malignant lymphoma, breast cancer, multiple myeloma and prostate cancer.

In the present invention, a combination of a medical agent containing the compound represented by the formula (I) or a pharmaceutically acceptable salt thereof and a medical agent containing lenalidomide or a pharmaceutically acceptable salt thereof, can be used for hematological cancers. Of the hematological cancers, malignant lymphomas and myelodysplastic syndromes are preferred hematological cancers to which the combination is applied. Of the malignant lymphomas, non-Hodgkin's lymphoma is preferred as a malignant lymphoma to which the combination is applied. In another aspect, the combination can be used for solid cancers such as lung cancer, gastric cancer, pancreatic cancer, colorectal cancer, osteosarcoma, breast cancer and pediatric cancer.

In the present invention, a combination of a medical agent containing the compound represented by the formula (I) or a pharmaceutically acceptable salt thereof and a medical agent containing bortezomib or a pharmaceutically acceptable salt thereof, can be used for, e.g., multiple myeloma and mantle cell lymphoma.

In the present invention, a combination of a medical agent containing the compound represented by the formula (I) or a pharmaceutically acceptable salt thereof and a medical agent containing erlotinib or a pharmaceutically acceptable salt thereof, can be used for, e.g., lung cancer and pancreatic cancer.

In the present invention, a combination of a medical agent containing the compound represented by the formula (I) or a pharmaceutically acceptable salt thereof and a medical agent containing lapatinib or a pharmaceutically acceptable salt thereof, can be used for, e.g., breast cancer and preferably a cancer where HER2 is excessively expressed.

In the present invention, a combination of a medical agent containing the compound represented by the formula (I) or a pharmaceutically acceptable salt thereof and a medical agent containing olaparib or a pharmaceutically acceptable salt thereof, can be used for, e.g., ovarian cancer and breast cancer, and preferably, a BRCA genetic mutation-positive cancer.

In the present invention, a combination of a medical agent containing the compound represented by the formula (I) or a pharmaceutically acceptable salt thereof and a medical agent containing vorinostat or a pharmaceutically acceptable salt thereof, can be used for, e.g., non-Hodgkin's lymphoma (including, for example, skin T cellular lymphoma).

In the present invention, a combination of a medical agent containing the compound represented by the formula (I) or a pharmaceutically acceptable salt thereof and a medical agent containing sorafenib or a pharmaceutically acceptable salt thereof, can be used for, e.g., kidney cancer (including, for example, renal cell cancer), liver cancer (including, for example, hepatocyte cancer) and thyroid cancer.

In the present invention, a combination of a medical agent containing the compound represented by the formula (I) or a pharmaceutically acceptable salt thereof and a medical agent containing quizartinib or a pharmaceutically acceptable salt thereof, can be used for, e.g., acute myelogenous leukemia, and preferably, a cancer having a FLT3-ITD mutation.

In the present invention, a combination of a medical agent containing the compound represented by the formula (I) or a pharmaceutically acceptable salt thereof and a medical agent containing venetoclax or a pharmaceutically acceptable salt thereof, can be used for hematological cancers. Of the hematological cancers, malignant lymphomas and myelodysplastic syndromes are preferred hematological cancers to which the combination is applied. Of the malignant lymphomas, non-Hodgkin's lymphoma is a preferred malignant lymphoma to which the combination is applied. In another aspect, the combination can be used for solid cancers such as lung cancer, gastric cancer, pancreatic cancer, colorectal cancer, osteosarcoma, breast cancer and pediatric cancer.

In the present invention, a combination of a medical agent containing the compound represented by the formula (I) or a pharmaceutically acceptable salt thereof and a medical agent containing ibrutinib or a pharmaceutically acceptable salt thereof, can be used for hematological cancers. Of the hematological cancers, malignant lymphomas are preferred hematological cancers to which the combination is applied. Of the malignant lymphomas, non-Hodgkin's lymphoma is a preferred malignant lymphoma to which the combination is applied.

In another aspect, the combination can be used for solid cancers such as lung cancer, gastric cancer, pancreatic cancer, colorectal cancer, osteosarcoma, breast cancer and pediatric cancer.

In the present invention, a combination of a medical agent containing the compound represented by the formula (I) or a pharmaceutically acceptable salt thereof and a medical agent containing panobinostat or a pharmaceutically acceptable salt thereof, can be used for, e.g., multiple myeloma.

In the present invention, a combination of a medical agent containing the compound represented by the formula (I) or a pharmaceutically acceptable salt thereof and a medical agent containing 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one or a pharmaceutically acceptable salt thereof, can be used for, e.g., gastric cancer, liver cancer, colorectal cancer, breast cancer, pancreatic cancer, cervical cancer, endometrial cancer, ovarian cancer, esophageal cancer, lung cancer and head and neck cancer.

In the present invention, a combination of a medical agent containing the compound represented by the formula (I) or a pharmaceutically acceptable salt thereof and a medical agent containing 5-{8-[(3R)-4-acetyl-3-methylpiperazin-1-yl]-6-morpholin-4-yl-9-(2,2,2-trifluoroethyl)-9H-purin-2-yl}pyrimidin-2-amine or a pharmaceutically acceptable salt thereof, can be used for, e.g., gastric cancer, liver cancer, colorectal cancer, breast cancer, pancreatic cancer, cervical cancer, endometrial cancer, ovarian cancer, esophageal cancer, lung cancer and head and neck cancer.

In the present invention, a combination of a medical agent containing the compound represented by the formula (I) or a pharmaceutically acceptable salt thereof and a medical agent containing milademetan or a pharmaceutically acceptable salt thereof, can be used for, e.g., gastric cancer, liver cancer, colorectal cancer, breast cancer, pancreatic cancer, cervical cancer, endometrial cancer, ovarian cancer, esophageal cancer, lung cancer, head and neck cancer and myelodysplastic syndrome.

In the present invention, a combination of a medical agent containing the compound represented by the formula (I) or a pharmaceutically acceptable salt thereof and a medical agent containing rituximab or a pharmaceutically acceptable salt thereof, can be used for hematological cancers. Of the hematological cancers, malignant lymphomas are preferred hematological cancers to which the combination is applied. Of the malignant lymphomas, non-Hodgkin's lymphoma is a preferred malignant lymphoma to which the combination is applied.

In the present invention, a combination of a medical agent containing the compound represented by the formula (I) or a pharmaceutically acceptable salt thereof and a medical agent containing an anti-PD-1 antibody, an anti-PD-L1 antibody or an anti-CTLA-4 antibody, can be used for hematological cancers. Of the hematological cancers, malignant lymphomas are preferred hematological cancers to which the combination is applied.

In another aspect, the combination can be used for solid cancers. Of the solid cancers, the composition is preferably used for skin cancer, gastric cancer, liver cancer, colorectal cancer, breast cancer, pancreatic cancer, cervical cancer, endometrial cancer, ovarian cancer, esophageal cancer, lung cancer, head and neck cancer and myelodysplastic syndrome.

In the present invention, a combination of a medical agent containing the compound represented by the formula (I) or a pharmaceutically acceptable salt thereof and medical agents involved in CHOP therapy, can be used for hematological cancers. Of the hematological cancers, malignant lymphomas are preferred hematological cancers to which the combination is applied. Of the malignant lymphomas, non-Hodgkin's lymphoma is a preferred malignant lymphoma to which the combination is applied.

In the present invention, a combination of a medical agent containing the compound represented by the formula (I) or a pharmaceutically acceptable salt thereof and medical agents involved in R-CHOP therapy, can be used for, e.g., hematological cancers. Of hematological cancers, malignant lymphomas are preferred hematological cancers to which the combination is applied. Of the malignant lymphomas, non-Hodgkin's lymphoma is a preferred malignant lymphoma to which the combination is applied.

In the present invention, the phrase "administered in combination" means that both types of medical agent are taken into the body of a subject within a predetermined period. A preparation containing both types of medical agent in a single formulation may be administered or two preparations containing respective types of medical agent may be administered separately. In the case of separate preparations, the timing of administration of them is not particularly limited. The preparations may be administered at the same time or different times with a time interval between them, or administered on different days.

If they are administered at different times or on different days, the order of administration is not particularly limited. Since the medical agents are administered in accordance with the administration methods respectively instructed, the administration times of them may coincide with each other or be mutually different. If they are separate preparations, the administration method (route of administration) of the preparations may be the same or different. Also, it is not necessary for the two types of medical agents to be present at the same time. It is sufficient that the two medical agents are taken and remain in the body for a certain period (for example, a month, preferably a week, further preferably a few days, even further preferably a day). Alternatively, when one of the preparations is administered, the other active ingredient may have disappeared from the body.

The pharmaceutical composition of the present invention may be used in combination with another antitumor agent and another therapy (for example, radiation therapy, immunotherapy).

In the present invention, "pharmaceutically acceptable salt" refers to a salt which has no significant toxicity and can be used as a pharmaceutical composition. A salt can be formed by reacting a compound having an acidic substituent with a base. Examples of the salt include, but are not limited to, alkali metal salts such as a sodium salt, a potassium salt and a lithium salt; alkaline earth metal salts such as a calcium salt and a magnesium salt; metal salts such as an aluminum salt and an iron salt; inorganic salts such as an ammonium salt; amine salts such as organic salts including a tert-butylamine salt, a tert-octylamine salt, a dibenzylamine salt, a morpholine salt, a glucosamine salt, a phenylglycine alkyl ester salt, an ethylenediamine salt, a N-methylglucamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzylphenethylamine salt, a piperazine salt, a tetramethylammonium salt and a tris (hydroxymethyl) amino methane salt; and amino acid salts such as a glycine salt, a lysine salt, an arginine salt, an ornithine salt, a glutamate and an aspartate.

A salt can be also formed by reacting a compound having a basic substituent with an acid. Examples of the salt include halide acid salts such as a hydrofluoride, a hydrochloride, a hydrobromide and a hydroiodide; inorganic acid salts such as a nitrate, a perchlorate, a sulfate and a phosphate; $C_1$-$C_6$ alkyl sulfonates such as methanesulfonate, trifluoromethanesulfonate and ethane sulfonate; arylsulfonates such as benzenesulfonate and p-toluenesulfonate; organic acid salts such as an acetate, a malate, a fumarate, a succinate, a citrate, an ascorbate, a tartrate, an oxalate, an adipate and a maleate; and amino acid salts such as a glycine salt, a lysine salt, an arginine salt, an ornithine salt, a glutamate and an aspartate.

In the present invention, when the compound represented by the formula (I), metabolic antagonist, alkylating agent, platinum preparation, antitumor antibiotic substance, antitumor plant component, hormonal agent, immunomodulator, molecular target drug and pharmaceutically acceptable salts of these medical agents are allowed to stand still in the air or recrystallize, they sometimes incorporate water molecule(s) to form hydrates. The hydrates are also included in the present invention.

In the present invention, when the compound represented by the formula (I), metabolic antagonist, alkylating agent, platinum preparation, antitumor antibiotic substance, antitumor plant component, hormonal agent, immunomodulator, molecular target drug and pharmaceutically acceptable salts of these medical agents are allowed to stand still in a solvent or recrystallize, they sometimes absorb the solvent to form solvates. Such solvates are also included in the present invention.

In the present invention, if the compound represented by the formula (I), metabolic antagonist, alkylating agent, platinum preparation, antitumor antibiotic substance, antitumor plant component, hormonal agent, immunomodulator, molecular target drug, immune checkpoint inhibitor and pharmaceutically acceptable salts of these medical agents are prepared into pharmaceutical compositions, examples of pharmaceutically acceptable carriers to be used in the compositions include, but are not limited to, sterilized water, saline, a vegetable oil, a solvent, a base, an emulsifier, a suspension, a surfactant, a stabilizer, a seasoning agent, an aromatic substance, an excipient, a vehicle, a preservative, a binder, a diluent, an isotonic agent, a soothing agent, a thickening agent, a disintegrant, a buffering agent, a coating agent, a lubricant, a colorant, a sweetener, a viscous agent, a flavoring agent and a dissolution aid (or other additives). The compound of the present invention or a pharmaceutically acceptable salt thereof may be formed into various dosage forms, such as a tablet, a powder, a granule, a capsule and a liquid, depending on the therapeutic purpose; and may be administered, for example, by a delivery system using liposomes. To the liposomes, the aforementioned auxiliary parts (e.g., antibody, a ligand) that enhance therapeutically useful properties can be added.

For administration to a patient, either oral administration or parenteral administration can be employed. Examples of parenteral administration include intravenous administration, intraarterial administration, intramuscular administration, intrathoracic administration, intraperitoneal administration and direct administration to a target site (for example, tumor).

The dosage amount is not particularly limited as long as it is an effective amount for treating a target disease and appropriately selected depending on the age, body weight, symptom, health condition and disease progression of the patient. The frequency of administration is not particularly limited and can be appropriately selected depending on the purpose. For example, the dosage amount per day is administered once a day or divided into a plurality of doses and administered separately. When the medical agent of the present invention is administered to a human, the dosage amount of an active ingredient ranges from about 0.01 mg/kg (body weight) to about 500 mg/kg (body weight), and preferably, about 0.1 mg/kg (body weight) to about 100 mg/kg (body weight). For administration to a human, the dosage amount per day is preferably administered once a day or divided into 2 to 4 portions, which are administered separately at appropriate intervals.

Note that, in the present invention, the compound represented by the formula (I), a metabolic antagonist, an alkylating agent, a platinum preparation, an antitumor antibiotic substance, an antitumor plant component, a hormonal agent, an immunomodulator, a molecular target drug, an immune checkpoint inhibitor and pharmaceutically acceptable salts of these medical agents may each be prepared into a reagent for use in assays and, if necessary, other components acceptable for use in assays, such as sterilized water, saline, a buffering agent and/or a preservative, can be added. The reagent is administered to a target (e.g., cells, fractionated cells, tissue, experimental animal) according to purpose, in a dosage amount in accordance with the purpose, to suppress the growth of a tumor.

EXAMPLES

The present invention will be more specifically described by way of Examples; however the scope of the present invention is not limited by these.

(Experimental Example 1) Evaluation of Cell Growth Inhibitory Activity by Combined Use of Compound A and a Second Medical Agent Cell strains listed in Table 1 and Table 2 were seeded in cell culture plates (for example, 6-well culture plates). DMSO solutions of Compound A diluted to different concentrations or DMSO alone were added such that the concentration of the solvent was 0.1%. The cells were cultured for 7 days. During the culturing, at intervals of about 3 days or 4 days depending on cell proliferation, subculturing was appropriately carried out. In the subculturing, DMSO solutions of Compound A diluted to different concentrations or DMSO alone were added to fresh medium at the same concentration as in initiation of the study.

The cell strains cultured in the above conditions were seeded in 96-well assay plates and the cells were cultured under a combination of the following conditions:

(i) DMSO solutions of Compound A diluted to different concentrations or DMSO alone were added such that the concentration of the solvent was 0.1%, and
(ii) DMSO solutions of a second medical agent or DMSO alone (if a preparation of a second medical agent was used, the preparation of the second medical agent was diluted with saline and used, or saline alone was used) was added such that the concentration of the solvent was 0.1%.

During the culturing period, the culture conditions were 37° C. and 5% $CO_2$. On the day when the cells were seeded in a 96-well assay plate (day of seeding) and 3 days later (day of evaluation), a reaction was carried out using Cell-Titer-Glo 2.0 Assay reagent (Promega KK., #G9241) in accordance with the manual attached thereto. Thereafter, the amount of light emitted from each of the wells was measured by a plate reader (EnVision, PerkinElmer Co., Ltd.). Based on the luminescence of the sample addition group (TS) and the DMSO addition group (CS) for each treatment condition measured on the day of seeding; and the luminescence of the sample addition group (T) and the DMSO addition group (C) for each treatment condition measured on the day of evaluation, the cell growth inhibition rate was calculated in accordance with the following expression:

Cell growth inhibition rate %={1−(T−TS)/(C−CS)}×100

Note that, if the number of cells of a sample addition group on the day of evaluation was lower than that of the day of seeding (T<TS), the cell-killing effect was calculated in accordance with the following expression:

Cell-killing rate %=(T−TS)/TS×(−100)

The cell growth inhibition rate and cell killing rate obtained by calculation were fitted to the Sigmoid Emax model to calculate 100% cell growth inhibitory concentration of each of Compound A alone, a second medical agent alone, and Compound A-second medical agent combinations at different concentrations.

Based on the 100% cell growth inhibitory concentrations (Compound A alone: D1, second medical agent alone: D2, Compound A when used in combination: d1, second medical agent when used in combination: d2) calculated, the combination index (CI) was calculated in accordance with the following expression:

CI=d1/D1+d2/D2

Determination was based on the criteria: if CI<1, a synergetic effect is present; if CI=1, an additive effect is present; and if CI>1, an antagonist effect is present (refer to Adv. Enzyme Regul. 1984, p. 2227-55).

The results are shown in Table 1 and Table 2. A synergetic effect was confirmed in all cancer types.

TABLE 1

| Cancer type | EZH2 | Cell strain | Cpd A $GI_{100}$ (nM) | Combination Index | | | | | | | |
|---|---|---|---|---|---|---|---|---|---|---|---|
| | | | | Cpd A + DOX | Cpd A + ETP | Cpd A + VCR | Cpd A + IBR | Cpd A + LEN | Cpd A + VEN | Cpd A + PAN | Cpd A + SN38 |
| DLBCL (GCB) | WT | DOHH-2 | 17 | 1 | 1 | 1 | 0.8 | 0.6 | 0.7 | 0.6 | 0.3 |
| | | OCI-LY7 | 90 | 1 | 0.8 | 2 | 0.5 | 0.5 | 1 | 0.5 | 0.4 |
| | | OCI-LY19 | >1000 | 0.4 | 0.4 | 0.6 | 0.9 | 1 | 0.4 | 0.6 | 0.6 |
| | MT (Y641N) | KARPAS-422 | 5.7 | 1 | 1 | 1 | 1 | 0.85 | 1 | 1 | 0.8 |
| | | DB | >100 | 0.5 | 0.3 | 0.4 | 0.9 | 1 | 0.4 | 0.7 | 0.5 |
| DLBCL (non-GCB) | WT | SU-DHL-2 | 4.9 | 1 | 1 | 1 | 0.7 | 1 | 0.5 | — | — |
| | | OCI-LY3 | >1000 | 0.4 | 0.4 | 0.7 | 1 | 0.1 | 0.1 | 0.5 | 0.9 |
| MCL | WT | JeKo-1 | 8.1 | 0.9 | 1 | 0.6 | 2 | 1 | 0.6 | — | — |
| | | GRANTA-519 | 53 | — | 1 | 1 | 1 | 1 | 0.2 | — | — |
| | | REC-1 | 170 | 0.8 | 0.9 | 0.9 | — | 0.8 | 0.8 | — | — |

DLBCL: diffuse large B-cell lymphoma,
GCB: germinal center B cell type,
MCL: mantle cell lymphoma,
WT: wild type,
MT: mutant,
$GI_{100}$: 100% cell growth inhibitory concentration,
DOX: doxorubicin,
ETP: etoposide,
IBR: ibrutinib,
LEN: lenalidomide,
VCR: vincristine,
VEN: venetoclax,
PAN: panobinostat,
SN38: active metabolite of irinotecan

TABLE 2

| Cancer type | Cell strain | Translocation/genetic mutation | Cpd A $GI_{100}$ (nM) | Combination Index | | |
|---|---|---|---|---|---|---|
| | | | | Cpd A + 5-Aza | Cpd A + Ara-C | Cpd A + VEN |
| AML | MOLM13 | MLL-AF9, FLT3-ITD | 97 | 0.3 | 0.8 | 0.6 |
| | MOLM14 | MLL-AF9, FLT3-ITD | >1000 | 0.5 | 0.7 | 0.3 |
| | MV-4-11 | MLL-AF4, FLT3-ITD | >100 | 0.3 | 0.4 | 0.3 |
| | OCI-AML2 | MLL-AF6, DNMT3Amt, FLT3-ITD | 647 | 1 | 0.6 | 0.7 |

TABLE 2-continued

| Cancer type | Cell strain | Translocation/genetic mutation | Cpd A GI$_{100}$ (nM) | Combination Index | | |
|---|---|---|---|---|---|---|
| | | | | Cpd A + 5-Aza | Cpd A + Ara-C | Cpd A + VEN |
| | OCI-AML3 | NPM1mt, DNMT3Amt | >1000 | NA | 0.8 | NA |
| | OCI-AML5 | — | >5000 | NA | 0.6 | 0.5 |

AML: acute myelogenous leukemia,
5-Aza: 5-azacytidine,
Ara-C: cytarabine,
VEN: venetoclax,
NA: fail to reach GI$_{100}$.

(Experimental Example 2) Evaluation of the Combined Effect of Compound A and CHOP Therapy on the KARPAS-422 Xenograft Model Human diffuse large B-cell lymphoma KARPAS-422 cells were transplanted into the subcutaneous tissue of the right abdomen of each female SCID mouse (Day 0). Twenty days later, the mice were divided into groups based on estimated tumor volumes (major axis×minor axis×minor axis/2). To the mice of a Compound A administration group, Compound A (dosage selection: 100 mg/kg/day) was orally administered once a day for 12 consecutive days from Day 21 to Day 32 (QD×12). To the mice of a CHOP therapy group, cyclophosphamide (dosage selection: 25 mg/kg), doxorubicin (dosage selection: 3 mg/kg), and vincristine (dosage selection: 0.25 mg/kg) were administered by tail vein injection once on Day 21 (QD×1); and prednisone (dosage selection: 0.3 mg/kg) was orally administered once a day for 5 consecutive days from Day 21 to Day 25 (QD×5). Also, a combination test was carried out by using these in combination. The results are shown in FIG. 1.

Compared to Compound A alone and CHOP therapy alone, a combination of Compound A and CHOP therapy exerted an excellent antitumor effect.

(Experimental Example 3) Evaluation of the Combined Effect of Compound A and R-CHOP Therapy on the KARPAS-422 Xenograft Model Human diffuse large B-cell lymphoma KARPAS-422 cells were transplanted into the subcutaneous tissue of the right abdomen of each female SCID mouse (Day 0). Twenty one days later, the mice were divided into groups based on estimated tumor volumes. To the mice of a Compound A administration group, Compound A (dosage selection: 100 mg/kg/day) was orally administered once a day for 11 consecutive days from Day 22 to Day 32 (QD×11). To the mice of an R-CHOP therapy group, rituximab (dosage selection: 10 mg/kg), was administered by tail vein injection once on Day 21 (QD×1); cyclophosphamide (dosage selection: 25 mg/kg), doxorubicin (dosage selection: 3 mg/kg) and vincristine (dosage selection: 0.25 mg/kg), were administered by tail vein injection once on Day 22 (QD×1); and prednisone (dosage selection: 0.3 mg/kg) was orally administered once a day for 5 consecutive days from Day 22 to Day 26 (QD×5). Also, a combination test was carried out by using these in combination. The results are shown in FIG. 2.

Compared to Compound A alone and R-CHOP therapy alone, a combination of Compound A and R-CHOP therapy exerted an excellent antitumor effect.

(Experimental Example 4) Evaluation of the Combined Effect of Compound A and Rituximab on the WSU-DLCL2 Xenograft Model Human diffuse large B-cell lymphoma WSU-DLCL2 cells were transplanted into the subcutaneous tissue of the right abdomen of each female SCID mouse (Day 0). Fifteen days later, the mice were divided into groups based on estimated tumor volumes. The mice of a Compound A administration group were allowed to take a feed mix containing 0.3% of Compound A at discretion for 28 consecutive days from Day 16 to Day 44 (QD×28). To the mice of a rituximab administration group, rituximab (dosage selection: 10 mg/kg) was administered by tail vein injection once on Day 15 (QD×1). Also, a combination test was carried out by using these in combination. The results are shown in FIG. 3. Compared to Compound A alone and rituximab alone, a combination of Compound A and rituximab exerted an excellent antitumor effect.

(Experimental Example 5) Evaluation of the Combined Effect of Compound A and an Anti-PD-1 Antibody, Anti-PD-L1 Antibody or Anti-CTLA-4 Antibody on the A20 Syngeneic Model The anti-PD-1 antibody, anti-PD-L1 antibody and anti-CTLA-4 antibody used herein were all manufactured by Bio X cell. Mouse B cellular lymphoma A20 cells were transplanted into the subcutaneous tissue of the right abdomen of each female Balb/c mouse (Day 0). To the mice of a Compound A administration group, Compound A (dosage selection: 100 mg/kg/day) was orally administered once a day for 18 consecutive days from Day 0 to Day 17 (QD×18). To the mice of an anti-PD-1 antibody administration group, an anti-PD-1 antibody (dosage selection: 5 mg/kg) was administered by tail vein injection on Day 0, 3 and 7. Also, a combination test was carried out by using these in combination. The results are shown in FIG. 4. To the mice of an anti-PD-L1 antibody administration group, an anti-PD-L1 antibody (dosage selection: 5 mg/kg) was administered by tail vein injection on Day 4, 8 and 11. Also, a combination test was carried out by using Compound A and the anti-PD-L1 antibody in combination. The results are shown in FIG. 5. To the mice of an anti-CTLA-4 antibody administration group, an anti-CTLA-4 antibody (dosage selection: 5 mg/kg) was administered by tail vein injection on Day 4, 8 and 11. Also, a combination test was carried out by using Compound A and the anti-CTLA-4 antibody in combination. The results are shown in FIG. 6. Compared to Compound A alone, the anti-PD-1 antibody, anti-PD-L1 antibody, and anti-CTLA-4 antibody alone, a combination of Compound A and each of the antibodies exerted an excellent antitumor effect.

(Experimental Example 6) Evaluation of the Combined Effect of Compound A and 5-Azacytidine on the MV-4-11 Xenograft Model Human acute myelogenous leukemia MV-4-11 cells were transplanted into the tail vein of each female NOG mouse (Day 0). To the mice of a Compound A administration group, Compound A (dosage selection: 120 mg/kg/day) was orally administered once a day for 18 consecutive days from Day 3 to Day 20 (QD×18). To the mice of a 5-azacytidine group, 5-azacytidine (dosage selection: 3.5 mg/kg) was administered by tail vein injection for 4 consecutive days from Day 7 to Day 10 (QD×4). Also, a combination test was carried out by using these in combination. The results are shown in FIG. 7.

Compared to Compound A alone and 5-azacytidine alone, a combination of Compound A and 5-azacytidine exerted an excellent life prolongation.

(Experimental Example 7) Evaluation of the Combined Effect of Compound A and Irinotecan on the NCI-H446 Xenograft Model Human small cell lung cancer NCI-H446 cells were transplanted into the subcutaneous tissue of the right abdomen of each female SCID mouse (Day 0). Twenty one days later, the mice were divided into groups based on estimated tumor volumes. To the mice of a Compound A administration group, Compound A (dosage selection: 100 mg/kg/day) was orally administered once a day for 18 consecutive days from Day 21 to Day 38 (QD×18). To the mice of an irinotecan (CPT-11) administration group, irinotecan (dosage selection: 60 mg/kg) was administered by tail vein injection once on Day 25 (QD×1). Also, a combination test was carried out by using these in combination. The results are shown in FIG. 8.

Compared to Compound A alone and irinotecan alone, a combination of Compound A and irinotecan exerted an excellent antitumor effect.

(Experimental Example 8) Evaluation of the Combined Effect of Compound A and Carboplatin on the NCI-H446 Xenograft Model Human small cell lung cancer NCI-H446 cells were transplanted into the subcutaneous tissue of the right abdomen of each female SCID mouse (Day 0). Twenty one days later, the mice were divided into groups based on estimated tumor volumes. To the mice of a Compound A administration group, Compound A (dosage selection: 100 mg/kg/day) was orally administered once a day for 18 consecutive days from Day 21 to Day 38 (QD×18). To the mice of a carboplatin (CBDCA) administration group, carboplatin (dosage selection: 50 mg/kg) was administered by tail vein injection once on Day 25 (QD×1). Also, a combination test was carried out by using these in combination. The results are shown in FIG. 9. Compared to Compound A alone and carboplatin alone, a combination of Compound A and carboplatin exerted an excellent antitumor effect.

The invention claimed is:

1. A method for treating cancer in a patient in need thereof, comprising
administering a compound represented by the following formula (I):

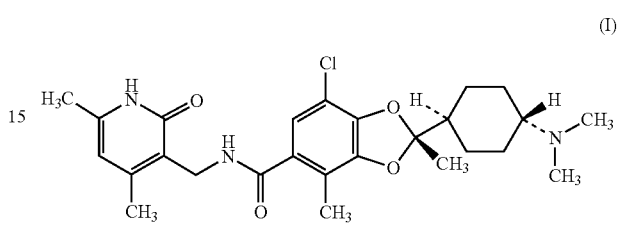

or a pharmaceutically acceptable salt thereof, and an immune checkpoint inhibitor in combination.

2. The method according to claim 1, wherein the compound represented by the above formula (I) or a pharmaceutically acceptable salt thereof and the immune checkpoint inhibitor are administered at the same time or different times.

3. The method according to claim 1, wherein the compound represented by the above formula (I) or a pharmaceutically acceptable salt thereof is a p-toluenesulfonate salt of the compound represented by the above formula (I).

4. The method according to claim 1, wherein the immune checkpoint inhibitor is at least one selected from an anti-PD-1 antibody, an anti-PD-L1 antibody or an anti-CLTA-4 antibody.

5. The method according to claim 1, wherein the immune checkpoint inhibitor is at least one selected from nivolumab, pembrolizumab, avelumab, atezolizumab, durvalumab or ipilimumab.

6. The method according to claim 1, wherein the cancer is hematological cancer.

7. The method according to claim 6, wherein the hematological cancer is non-Hodgkin's lymphoma.

8. The method according to claim 6, wherein the hematological cancer is acute myelogenous leukemia.

9. The method according to claim 6, wherein the hematological cancer is multiple myeloma.

10. The method according to claim 1, wherein the cancer is a solid cancer.

* * * * *